United States Patent
Kostenis et al.

(10) Patent No.: US 7,169,612 B2
(45) Date of Patent: Jan. 30, 2007

(54) USE OF EDG2 RECEPTOR IN AN ANIMAL MODEL OF HEART FAILURE

(75) Inventors: Evi Kostenis, Grebenau (DE); Paulus Wohlfart, Bensheim (DE); Jochen Huber, Maxdorf (DE); Kai Rosport, Munich (DE); Andreas Bueltmann, Munich (DE); Christine Baumgartner, Munich (DE); Götz Muench, Munich (DE); Martin Ungerer, Munich (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 206 days.

(21) Appl. No.: 10/706,763

(22) Filed: Nov. 12, 2003

(65) Prior Publication Data

US 2004/0132182 A1    Jul. 8, 2004

Related U.S. Application Data

(60) Provisional application No. 60/455,231, filed on Mar. 17, 2003.

(30) Foreign Application Priority Data

Nov. 11, 2002   (EP) .................................. 02025161

(51) Int. Cl.
| | |
|---|---|
| *C12N 5/16* | (2006.01) |
| *C12N 5/18* | (2006.01) |
| *C12N 15/65* | (2006.01) |
| *C12N 15/861* | (2006.01) |

(52) U.S. Cl. ...................... 435/456; 435/325; 435/353; 435/354

(58) Field of Classification Search .................... None
See application file for complete search history.

(56) References Cited

FOREIGN PATENT DOCUMENTS

| WO | WO 99/19513 | 4/1999 |
|---|---|---|
| WO | WO 00/11166 | 3/2000 |

OTHER PUBLICATIONS

An et al., "Molecular cloning of teh human Edg2 protein and its identification as a functional cellular receptor for lysophosphatidic acid," Biochem. Biophys. Res. Commun. 231:619-622, 1997.*

Goetzl et al., "Gelsolin binding and cellular presentation of lysophosphatidic acid," J. Biol. Chem. 275(19): 14573-14578, 2000.*

Kawada et al., "Precise identification of gene products in hearts after in vivo gene transfection, using Sendai virus-coated proteoliposomes," Biochem. Biophys. Res. Commun. 259 : 408-413, 1999.*

Karliner, Joel S. et al., The Lysophospholipids Sphingosine-1-Phosphate and Lysophosphatidic Acid Enhance Survival during Hypoxia in Neonatal Rat Cardiac Myocytes, J. Mol. Cell Cardiol., (2001), vol. 33, pp. 1713-1717.

* cited by examiner

*Primary Examiner*—Scott D. Priebe
(74) *Attorney, Agent, or Firm*—Xuhong Sunny Wang

(57) ABSTRACT

Mammals and myocardial mammal cells transformed with G protein coupled receptor EDG2 are presented for use in an animal model for heart failure.

7 Claims, 4 Drawing Sheets

USE OF EDG2 RECEPTOR IN AN ANIMAL MODEL OF HEART FAILURE

This application claims benefit to provisional application 60/455,231, filed Mar. 17, 2003, and European Patent Application No. 02025161.7, filed Nov. 11, 2002, published as EP1418185.

FIELD OF THE INVENTION

The invention refers to a transient transformed mammal which is useful as animal model for heart failure.

BACKGROUND OF THE INVENTION

G protein-coupled receptors (GPCRs) play a central role in a multiplicity of physiological processes. It is assumed that in the human genome about 1000 genes code for this receptor family. Approximately 60% of the pharmaceuticals presently available through prescription act as GPCR agonists or antagonists. This underlines the importance of this receptor class for the pharmaceutical research industry. Owing to the size and importance of said protein family and in view of the fact that physiological ligands are still unknown for many GPCRs (orphan GPCRs), it can be assumed that this receptor class will be one of the most important reservoirs for suitable target proteins in the search for novel medicinal substances in the future.

GPCRs are a family of integral membrane proteins which are located on cell surfaces. They receive signals from extracellular signaling substances (e.g. hormones, neurotransmitters, peptides, lipids) and transfer these signals into the cell interior via a family of guanine nucleotide-binding proteins, the "G proteins". Depending on the receptor specificity, the G protein activated and the cell type, these receptors induce various signal transduction pathways.

All GPCR polypeptide chains fold into seven $\alpha$-helices which span across the phospholipid bilayer of the cell membrane. The seven membrane passages result in the formation of extra- and intracellular loops which allow extracellular ligand binding and intracellular coupling of G proteins. For this reason, GPCRs are also denoted seven-pass transmembrane receptors.

All G protein-coupled receptors act according to a common basic pattern: binding of an extracellular ligand leads to a conformational change in the receptor protein which enables the receptor protein to contact a G protein. G protein-mediated signal transduction cascades in the cell finally lead to a biological response of the cell.

G proteins are heterotrimeric proteins which consist of the subunits $\alpha$, $\beta$ and $\gamma$. They are located on the inside of the cell membrane via lipid anchors. Coupling of activated GPCRs to G proteins induces a GDP/GTP exchange at the $G\alpha$ subunit and dissociation of the heterotrimeric G protein into an $\alpha$ and a $\beta\gamma$ subunit. Both the activated $\alpha$ subunit and the $\beta\gamma$ complex are able to interact with intracellular effector proteins.

Activation of membrane-bound adenylate cyclase (AC) by $G\alpha s$-type G proteins, for example, leads to an increase in the intracellular cAMP level or, in the case of activation by $G\alpha i$-type G proteins, to the decrease therein. Gq-type G proteins activate phospholipase C (PLC) which catalyzes the formation of inositol 1,4,5-triphosphate (IP3) and diacylglycerol (DAG). These molecules lead to the release of $Ca^{2+}$ from intracellular storage organelles or to activation of proteinkinase C (PKC).

The polynucleotide sequence and the amino acid sequence of the human EDG2 (Endothelial Differentiation Gene 2) has been made available to the public. The sequence is available for example from NCBI (Accession: NM_001401). The protein sequence is available from Swiss Prot (Accession: Q 92633). Cloning of the receptor from a human lung cDNA library was published in "An et al., Biochem. Biophys. Res. Commun. 24, 231 (1997)".

The full length sequence encodes a 359 amino acid protein which belongs to the superfamily of guanine nucleotide-binding protein-coupled receptors (GPCR). Human EDG2 mRNA is widely distributed in human tissues with the highest abundance in brain. HEK293 cells expressing the human EDG2 protein showed an elevated response to lysophosphatidic acid (LPA) in a serum response element reporter gene assay, which was LPA concentration dependent and specific to LPA. The mouse counterpart of EDG2 protein was also identified as a receptor for LPA.

Lysophosphatidic acid (LPA) and sphingosine 1-phosphate (S1P) are potent phospholipid mediators with diverse biological activities. Their appearance and functional properties suggest possible roles in development, wound healing, and tissue regeneration. The growth-stimulating and other complex biological activities of LPA and S1P are attributable in part to the activation of multiple G protein-mediated intracellular signaling pathways. Several heterotrimeric G proteins, as well as Ras- and Rho-dependent pathways play central roles in the cellular responses to LPA and S1P.

DESCRIPTION OF THE INVENTION

Figure 1:
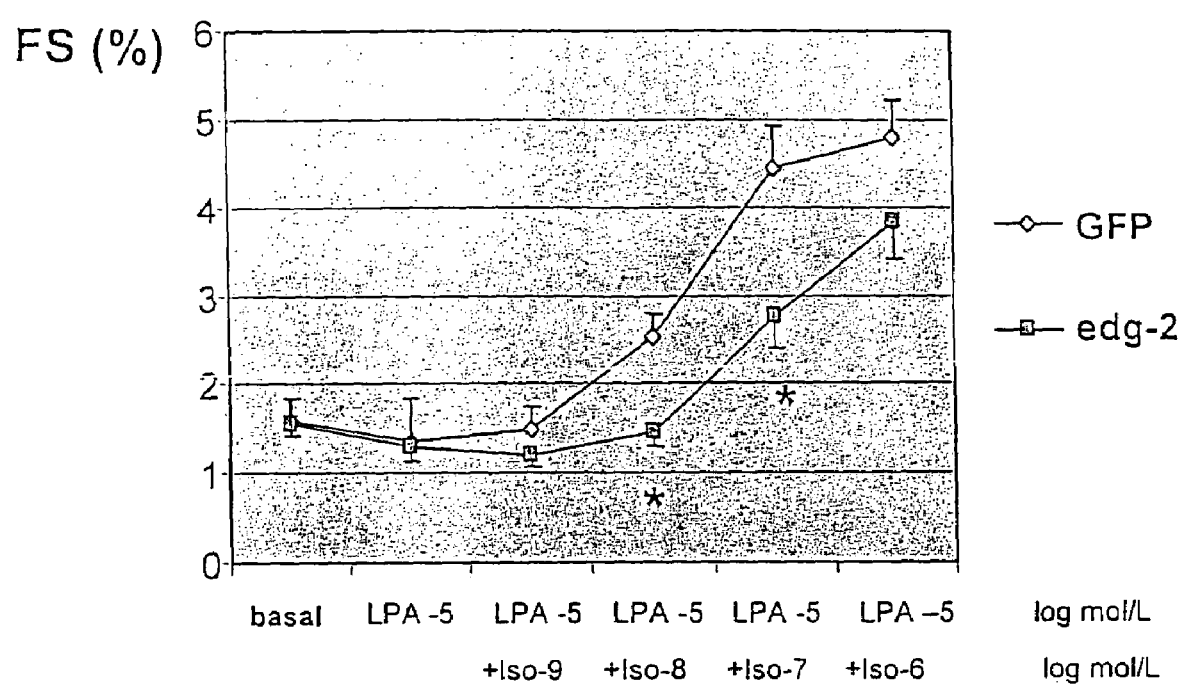
FIG. 1:
Contraction amplitude of single cardiomyocytes isolated from failing hearts. The cardiomyocytes were infected ex vivo with either Ad-GFP or Ad-EDG2-GFP. Fractional shortening (FS) was determined in response to increasing concentrations of isoproterenol after prestimulation with 10 µM of LPA. Data represent means±SEM.

Within the scope of this invention and in all cases used and without any exemption, "mammal" and "mammalian"

shall not encompass the human species (*Homo sapiens*) or an individual of *Homo sapiens* of part of a body of a human.

Within the scope of this invention and in all cases used and without any exemption, "cellular marker" is defined as a protein which is detectable by some laboratory method once a mammalian cell is transformed with a nucleotide sequence encoding that protein. Examples of cellular markers include beta galactosidase and fluorescent proteins, such as Green Fluorescent Protein (GFP), Reef Coral Fluorescent Proteins or the like. One of skill in the art of mammalian molecular biology has ready access to such cellular marker proteins and nucleotide sequences and is capable of marking transfection or transformation of a mammalian cell with them using standard laboratory techniques.

The invention refers to a myocardial cell of a mammal, which cell contains an adenoviral vector sequence for simultaneous expression of a G protein coupled receptor EDG2 and a cellular marker, such as Beta-Galactosidase or a fluorescent protein such as GFP.

The adenoviral vector sequence consists preferably of a recombinant E 1/E 3 deficient adenovirus which expresses the G protein coupled receptor EDG2 and the celluluar marker under control of two independent promoters. Such promoters could be two CMV promoters.

The myocardial cell of a mammal which contains an adenoviral vector sequence as aforementioned expresses the G protein coupled receptor EDG2 and the cellular marker and contains therefore protein of the G protein coupled receptor EDG2 and the cellular marker.

The myocardial cell which contains an adenoviral vector sequence is preferably the cell of a rabbit, a mouse or a rat.

The invention refers also to production of a myocardial cell which cells contains an adenoviral vector sequence for simultaneous expression of G protein coupled receptor EDG2 and a cellular marker, wherein
a] the heart of a mammal is removed by state of the art veterinary medicine operative techniques,
b] the heart is perfused and digested with collagenase,
c] the isolated cardiomyocytes are infected with an adenoviral vector consisting of a recombinant E1/E3 deficient adenovirus which allows for expression of the G protein coupled receptor EDG2 and the cellular marker under control of two independent promoters. Such promoters are preferably two CMV promoters.

Furthermore the invention refers to a mammal having a myocardium which contains an adenoviral vector for simultaneous expression of a G protein coupled receptor EDG2 and a cellular marker. This adenoviral vector sequence of the mammals consists preferably of a recombinant E1/E3 deficient adenovirus which allows for expression of the G protein coupled receptor EDG2 and the cellular marker under control of two independent promoters. Such two independent promoters are preferably two CMV promoters.

The invention refers also to a mammal having a myocardium which contains a protein of G protein coupled receptor EDG2 and a protein of a cellular marker. Such a mammal having a myocardium with an adenoviral vector for simultaneous expression of a G protein coupled receptor EDG2 and a cellular marker and/or having a myocardium with protein of G protein coupled receptor EDG2 and protein of cellular marker is preferably a rabbit, a mouse, or a rat.

Furthermore the invention refers to production of a mammal having a myocardium with an adenoviral vector for simultaneous expression of a G protein coupled receptor EDG2 and a cellular marker and/or having a myocardium with protein of G protein coupled receptor EDG2 and protein of a cellular marker, wherein a] an adenoviral vector sequence for simultaneous expression of G protein coupled receptor EDG2 and a cellular marker is provided,
b] a mammal is provided,
c] the adenoviral vector system from a] is transferred into the myocardium of the mammal from b] by means of a catheter.

The invention concerns also use of a mammal having a myocardium with an adenoviral vector for simultaneous expression of a G protein coupled receptor EDG2 and a cellular marker and/or having a myocardium with protein of G coupled receptor EDG2 and protein of a cellular marker for producing myocardial cells which can be taken for a method for identification of a compound which modifies the activity of G protein coupled receptor EDG2.

The invention refers to a method for identification of a compound which modifies the activity of receptor EDG2 wherein
a] a transformed cell from a heart muscle which expresses the receptor EDG2 or a fusion protein comprising the receptor EDG2 is provided,
b] optionally, a treatment of the cell from a] is performed by use of isoproterenol and/or lyophosphatidic acid,
c] a chemical compound is provided,
d] the cell from a] or b] is brought in contact with the chemical compound from c],
e] the contractility of a cell from d] is determined and is brought in relation to the contractility of a cell which has the same characteristics as a cell from a] but which has not brought in contact with a chemical compound from c] and wherein a relative enhancement or reduction of contractility of the cell which has brought in contact with a chemical compound according to d] by this compound demonstrates the ability of such compound to modify the activity of receptor EDG2.

The invention refers furthermore to a method for identification of a compound which modifies the activity of receptor EDG2, wherein
a] a transformed cell from a heart muscle which expresses the receptor EDG2 or a fusion protein comprising the receptor EDG2 is provided,
b] optionally, a treatment of the cell from a] is performed by use of proterenol and/or lysophosphatidic acid,
c] a chemical compound is provided,
d] the cell from a] or b] is brought in contact with the chemical compound from c],
e] the contractility of a cell from d] is determined and is brought in relation to contractility of a cell of same cell type as a cell according to a] but which does not express a receptor EDG2 or a fusion protein comprising a receptor EDG2 wherein a relative enhancement or reduction of contractility of the cell which expresses a receptor EDG2 or a fusion protein comprising a receptor EDG2 by a compound demonstrates the ability of such compound to modify the activity of receptor EDG2.

The invention refers furthermore to an adenoviral vector consisting of one polynucleotide of the following groups:
a] a polynucleotide having a sequence as specified in SEQ ID NO. 5,
b] a polynucleotide which is 95% identical to the polynucleotide of SEQ ID NO. 5, and
c] a polynucleotide which is at least of the same length as the polynucleotide of SEQ ID NO. 5 and which hybridizes to a polynucleotide of SEQ ID NO. 5 when applying highly stringent hybridization conditions.

The adenoviral vector sequence encompasses preferably a polynucleotide sequence encoding a protein of amino acids 1-364 of SEQ ID NO. 2. The adenoviral vector sequence most preferably encompasses a polynucleotide sequence encoding the protein of SEQ ID NO. 2.

Hybridization means assembly of two single polynucleotide strains which have complementary sequences to double stands. Hybridization might occur between two DNA-strand, one DNA- and one RNA-strand as well as between two RNA-strands. Forming of hybrid polynucleotide strands may start from a solution which contains double stranded polynucleotide molecules by heating this solution to separate the double strands in single stranded polynucleotides. The heating step could consist of boiling in a water bath during 10 to 20 minutes. When the solution is slowly cooled down to room temperature after it was heated the hybridization to double stranded molecules will occur. Under experimental conditions the hybridization is commonly carried out by means of hybridization filters which polynucleotides have been fixed upon by blotting or electrophoresis. Hybridization might be visualized by use of complementary polynucleotide molecules which carry a radioactive or fluorescenic label. Stringency describes the degree of correspondence under certain conditions. The demands with respect to correspondence are higher under high stringent conditions. Under circumstance of hybridization of nucleic acids the stringency conditions are adjusted in dependence of participating nucleic acids as well as use and objective. The conditions for a highly stringent hybridization are such that only very well fitting complementary molecules are able to hybridize. A very well fitting complementary polynucleotide exhibits for example a degree of identity of 90, 91, 92, 93, 94, 95, 96, 97, 98, 99% with respect to the complementary partner molecule. Under low stringency hybridization occurs also between polynucleotide molecules which are only complementary within certain segments of the molecule or which have large sections with mismatched or unpaired base pairs.

A hybridization condition of high stringency could be a hybridization wherein the hybridization step in presence of a labeled probe will be carried out in an aqueous 2×SSC solution at 68° C. during at least 2 hours, and the following washing steps consist of a first washing in 2×SSC/0.1% SDS at room temperature for 5 minutes, a second washing in 1×SSC/0.1% SDS at 68° C. for 1 hour, and a third washing in 0.2% SSC/0.1% SDS at 68° C. for another hour.

A 2×SSC-, 1×SSC-, or 0.2×SSC solution is obtained by dilution of a 20×SSC solution. A 20×SSC solution consists of 3 mol/l NaCl and 0.3 mol/l Na-Citrate. The skilled person is well known of other standard methods for hybridization of polynucleotides under stringent conditions. Advice is given to him in particular by textbooks as "Current Protocols in Molecular Biology (Wiley Interscience; ISBN: 0-471-50338-X; eds.: F. M. Ansubel, R. Brant, R. R. Kingston, D. J. Moore, J. G. Seidmann, K. Struhl).

The invention consists further of use of an adenoviral vector consisting of one polynucleotide of the following groups:
a] a polynucleotide having a sequence as specified in SEQ ID NO. 5,
b] a polynucleotide which is 95% identical to the polynucleotide of SEQ ID NO. 5, and
c] a polynucleotide which is at least of the same length as the polynucleotide of SEQ ID NO. 5 and which hybridizes to a polynucleotide of SEQ ID NO. 5 when applying highly stringent hybridization conditions for constructing of transgenic mammals wherein the G protein coupled receptor EDG2 is transiently or permanently expressed in at least one tissue. Such a tissue is preferably a part of the heart of the mammal. Tissue could also consist of a part of brain, muscle, fat, liver, kidney or other organs of a mammal.

General technical aspects of the invention will be further explained within the following paragraphs.

Adenoviruses can infect a wide variety of cell types and tissues in both dividing and non-dividing cells. This characteristic, together with their relative ease of preparation and purification, has led to their extensive use as gene vectors.

The virus can incorporate only about 2 kb of foreign DNA without significant affects on its stability or its infectivity. The introduction of longer sequences therefore requires the removal of some or all of the virus genes. There are a range of techniques for constructing recombinant adenoviruses.

Vectors can be utilized for (amongst other things): (i) cancer therapy to deliver genes that will lead to tumor suppression and elimination; (ii) gene therapy, i.e. to deliver genes to tissues to augment defective genes; (iii) supplementary therapy to deliver genes, expression of which will combat disease processes.

In the first generation of vectors, the E1 and/or E3 gene cassettes were removed, allowing the introduction of up to 6.5 kb of foreign DNA, often under the control of a heterologous promoter. In the case of the E1 deletions, care was taken to ensure the retention of the ITR and the packaging sequences. Removal of the E1 region had the additional apparent advantage of impairing the transcription of the E2 genes (which are E1 dependent) and consequently the replication of virus DNA and the production of the virus capsid proteins.

The defective E1 viruses could be propagated by infection of 293 cells, which provide the E1 gene products in trans. Although many of the initial studies in vitro provided much promise, it soon became evident that the expression of the transgene in vivo was only transient and was depressed because of the overwhelming immune response, mounted mainly against the virus capsid antigens as well as the expressed transgene. One of the reason for this was the observation that many cells harbored E1-like proteins that allowed the E2 genes to function, albeit at reduced levels. In turn, this facilitated virus DNA replication and the synthesis of the late structural antigens and the production of replication-competent adenovirus (RCA). It also became evident that, at higher m.o.i., the E1 dependence of E2 gene transcription could be ablated.

The next approach was to construct vectors (using suitable complementing cell lines) with some or all of the E2 genes excised and hence with the capacity to replicate virus DNA and to produce RCAs removed. Generation of RCAs could also be prevented by constructing cell lines that do not contain adenovirus sequences that overlap those in the vector. Nevertheless, the host immune response was still a major impediment to achieving persistent transgene expression and was particularly evident when repeated infections were attempted. A number of studies confirmed that the infecting recombinant virus itself was sufficient to induce the immune response, perhaps not surprising in view of the early activation of signaling cascades noted above and the potent antigenicity of the capsid components.

Other, rather more sophisticated vectors (third generation) have been constructed by deleting other virus genes (Amalfitano et al. 1988) and the latest of these have all or nearly all of the virus genes removed. These so-called 'gutless' vectors (Hardy et al., 1997) originally retained only the ITR and packaging sequences and required helper virus and appropriate complementing cells for propagation, followed by careful purification. Nevertheless, there were problems associated with these techniques, mainly due to contaminating helper virus and vector instability. A further development, which prevented the packaging of the helper virus, involved the use of the Cre-lox helper-dependent system.

The AdEasy™ system for the production of recombinant adenoviruses is commercially available from Qbiogene. The construction of a recombinant adenovirus is typically a two-step process in which the desired expression cassette is first assembled into a transfer vector, and subsequently transferred into the adenoviral genome by homologous recombination. Insertion of DNA by homologous recombination is the most efficient way of introducing a gene into an adenovirus vector for two reasons: 1) adenoviral DNAs are large, linear molecules that contain sites for almost all restriction enzymes and 2) the genome is too large (36 kb) to be easily manipulated.

With the AdEasy™ vector system, the backbone vector containing most of the adenoviral genome is used in super coiled plasmid form rather than as linear DNA. The homologous recombination step is performed in *Escherichia coli*. In the AdEasy™ system the cDNA of interest is first cloned into a transfer vector. The resulting plasmid is then linearized with Pme I and co-transformed into *E. coli* strain BJ5183 together with pAdEasy-1, the viral DNA plasmid. The pAdEasy-1 is E1 and E3 deleted; its E1 functions can be complemented in 293A cells. Recombinations are selected with kanamycin and screened by restriction enzyme analysis. The recombinant adenoviral construct is then cleaved with Pac I to expose its ITR (Inverted Terminal Repeat) and transfected into QBI-293A cells to produce viral particles.

The homologous recombination step is mediated between a linearized transfer vector and an intact super coiled adenovirus plasmid. The kanamycin resistance gene present in the transfer vector allows for the selection of recombinants. Because the cleaved AdEasy™ transfer vectors yield only a low background of kanamycin-resistant colonies, the homologous recombination system has a high signal-to-noise ratio. The *E. coli* strain BJ5183 is not recA but is deficient in other enzymes that mediate recombination in bacteria and was selected for its higher efficiency of transformation and recombination capabilities. One recombination is achieved and verified, the adenoviral recombinant DNA can simply the transferred to a regular recA, endA strain such as DH5α for greater yields of DNA production. Due to its recA status, DH5α cannot be used to generate adenovirus recombinants by homologous recombination.

Green fluorescent protein (GFP) from Aequora victoria has rapidly become a standard reporter in many biological systems. GFP is unique among light-emitting proteins in that it does not require the presence of cofactors or substrates for the generation of light. In the jellyfish Aequora victoria GFP is acting in a calcium-dependent manner. When $Ca^{+2}$ binds another bioluminescent protein, aequorin, which transfers energy indirectly to GFP to trigger the release of green light. This energy transfer can be mimicked experimentally by exposure of GFP to standard long-wave ultraviolet light. There are GFP isoforms available which emit blue or red light and which are stable at elevated temperatures. GFP was first used to look into living cells by fluorescence microscopy to monitor protein localization and to visualize dynamic cellular events. A fusion between any cloned gene of interest and GFP can be produced by subcloning techniques and may be introduced into the organism of interest by transient or stable expression. The fate of the resulting protein inside the living cell can then be followed using conventional fluorescence microscopy. Detection does not require fixation or permenbilization of cells. Likewise a protein may be traced within an animals tissue by simultaneously expressing such protein and GFP.

Providing a cell includes its preparation, cultivation and further processing. Cells are provided, for example, by preparing suitable cell material from organs or tissues or by propagating suitable cell lines or microorganisms. Various suitable culture media can be used for cultivation. The cells are maintained at the optimum temperature for the organism. Where appropriate, preservatives, antibiotics, pH indicators, blood serum components, blood serum, auxiliaries or other substances are added to the growth medium used in each case. Processes for preparation, cultivation and further processing are described in standard textbooks (Example: Basic Cell Culture; Ed. J. M. Davis; IRL Press; 1994).

The application of recombinant techniques provides for a construct, which is to be expressed in a cell, to be present in the form of a polynucleotide sequence which can be prepared by a skilled worker in a routine manner with the aid of his specialist knowledge. The worker skilled in molecular biology/biochemistry can find the specialist knowledge for this, for example, in F. M. Ausubel et al.; Current Protocols in Molecular Biology; John Wiley & Sons; New York. A vector construct is prepared by incorporating a polynucleotide coding for the amino acid sequence of, for example, a GPCR into an expression vector. An expression vector is a vector in which a polynucleotide sequence can be expressed in a host cell into a protein. Vectors may be derived from plasmids, viruses or cosmids and must be capable of autonomous replication. They generally contain an origin of replication, cleavage sites for restriction enzymes and marker genes such as, for example, antibiotic resistance genes. In an expression vector, the polynucleotide sequence which is to be propagated or which has been introduced from the outside is under the functional control of a promoter. A promoter is a functional polynucleotide sequence of variable length, which is used to control transcription, i.e. synthesis of mRNA of a polynucleotide sequence immediately 3'—of said promoter. There are promoters which are active only in procaryotes, such as, for example, the lac, tac and trc promoters, and also promoters which are active only a eukaryotes, such as, for example, CMV or ADH promoters. In a preferred embodiment, the recombinant vector construct comprises an expression vector usable in eucaryotes and/or procaryotes. An expression vector contains a promoter which can be linked functionally to a polynucleotide sequence so that a protein encoded by said polynucleotide sequence is synthesized in an organism, for example a bacterium, fungus or the cell of a eucaryotic cell line. The promoter may be inducible, by means of tryptophan for example, or may be constitutively active. Examples of expression vectors are pUC18, pUC19, pBluescript, pcDNA3.1 etc.

Transfection is the introduction of foreign polynucleotide sequences into a host cell by means of a vector, and the subsequent propagation of said polynucleotide sequence to any number of identical copies.

A cell line is transiently transfected with a recombinant construct by means of routine methods which can be found by the skilled worker in the abovementioned Current Protocols in Molecular Biology, published by John Wiley & Sons, New York, or in Sambrook et al.; A Laboratory Manual, Cold Spring Harbor Laboratory, ISBN 0-87969-309-6. Examples of such routine methods are electroporation, $Ca^{2+}$-phosphate coprecipitation and transfection by means of liposomes. The transfected genes may be expressed in the host cell by Western blotting of cell lysates of transfected cells in combination with an immunological detection method. For this too, the required laboratory protocols can be found by the skilled worker in the manuals mentioned above. Specific antibodies for immunodetection of GPCR receptors, which are suitable for carrying out the method of the invention, are commercially available.

A chemical compound is provided in particular by chemical synthesis or isolation of chemical substances from biological material.

The skilled worker may use routine methods for chemical synthesis of a compound or isolation of a substance from cells. Such methods are available to the skilled worker in textbooks such as Organic Synthesis Workbook; 1995; John Wiley & Sons; ISBN 3-527-30187-9, The Organic Chemistry of Drug Synthesis; 1998; John Wiley & Sons; ISBN 0-471-24510-0, or Bioactive Compounds from Natural Sources; 2001; Taylor & Francis; ISBN 0-7484-0890-8.

The compounds obtained by synthesis or isolation may be dissolved in a suitable solvent. Suitable solvents may contain water, buffer substances (e.g. Tris, HEPES, MOPS, etc.), monovalent and/or divalent ions (e.g. $K^+$, $Na^+$, $Mg^{2+}$, $Ca^{2+}$, etc.), acids (e.g. HCl, $H_2SO_4$, formic acid, acetic acid, etc.), bases (e.g. NaOH, etc.), alcohol (e.g. methanol, ethanol, glycerol), detergents (e.g. Na dodecyl sulfate, etc.), organic solvents (e.g. formamide, acetone, dimethyl sulfoxide, etc.) and other components, in particular solubilizers and stabilizers.

The skilled worker can contact the chemical compound with said cell line by using laboratory routine methods. Contacting may take place, for example, in Erlenmeyer vessels, tubes, Eppendorf vessels or on microtiter plates. Temperature-controlled incubators for which a constant temperature of, for example, 30° C. or 37° C. and fixed $CO_2$ or humidity conditions can be set may be used for said contacting. Contacting may in particular also be carried out in laboratory robot devices provided therefore (FLIPR). Contacting is possible for different periods of time, from a few seconds to minutes and up to several hours. The conditions to be chosen in each case depend on the receptor, the cell line and the chemical compound.

The final form of a pharmaceutical relates to the final formulation, for example, as tablet, granules, spray, solution, ointment, tincture or other formulation forms.

Processing to the final form refers to the preparation of the particular formulation in generally, the daily dose is in the range from 0.3 mg to 100 mg (typically from 3 mg to 50 mg) per day and per kilogram of body weight, for example, 3–10 mg/kg/day. An intravenous does may be, for example, in the range from 0.3 mg to 1.0 mg/kg and can most suitably be administered as in infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active substance. It is thus possible for ampoules for injections to contain, for example, from 1 mg to 100 mg, and for single-dose formulations which can be administered orally, such as, for example, tablets or capsules, to contain, for example, from 1.0 to 1000 mg, typically from 10 to 600 mg.

EXAMPLES

The following examples of the invention are disclosed as illustrations of the invention, without restricting the invention to the scope of these examples.

Description of the Experimental Animals:

The animals employed for the studies are ten-week-old female New Zealand white rabbits supplied by Asamhof, Kissing (Germany). At the start of the study the animals have a body weight of between 2.7 and 3.3 kg.

Rearing and Housing Conditions of the Experimental Animals:

The young are weaned at 30 days. To minimize weaning stress the dam is separated from the young so that the litter initially remains together. After about 10–14 days the young are housed in pairs in fattening cages (l×b×h=28.5×60×34 cm) and then after about two weeks they are housed singly. The fatteners are introduced and removed in accordance with the "All in-All out" system to facilitate cleaning and disinfection.

The feed is produced in the in-house agricultural plant and is available to the rabbits ad libitum, as is drinking water.

Climate: The ventilation rate is 10,000 $m^3/h$ in summer and 3000 $m^3/h$ in winter. Particular attention is paid to avoiding drafts. In cold weather the temperature is maintained at about 15° C.; overheating of the animal house in summer is prevented as far as possible. Young weaners are kept at about 19° C. Ammonia in the animal house is to be kept below 30 ppm, relative humidity below 70%. The breeding house is illuminated for 16 hours at an intensity of about 20 lux.

Study Animal Housing:

The rabbits are brought in an air conditioned vehicle directly to the company, where they are allowed an adaptation period of 2 to 3 days to acclimatize themselves to the new diet and environment.

The rabbits are kept in conventional cages. The cage material consists of stainless steel with PVC inserts; the cage floor has an area of 4040 $cm^2$ and takes the form of a perforated bottom plate. The feces trays are cleaned daily and the cages are washed and hot-air-sterilized weekly. They are kept under constant conditions at a room temperature between 18 and 21° C. and a relative humidity of 55±5%. As the animal house has windows the illumination corresponds to the natural night-day cycle with an intensity of at least 100 lux.

Anesthesia and Preparation for Surgery:

On the first day of the study, feed and water are available ad libitum to the rabbits until the start of anesthesia. Then the designated animal is weighed and undergoes a clinical examination, particularly of the cardiovascular system and the respiratory tract. The animals are provided with double intravenous access via indwelling catheters in the left and right lateral auricular veins (Venflon™ 08.×25 mm), through which anesthesia is then induced with 1% propofol (Disoprivan, Fresenius AG, Bad Homburg) in a dose of 7 mg/kg body weight i.v. Eye ointment (Vitamin A Dispersa, Ciba Vision®, Grossostheim) is applied to the cornea immediately after induction of anesthesia. After disappearance of the righting reflex the rabbits are shaved ventrally on the neck and on the chest between the elbows and the last rib and are then incubated by advancing a Magill tube with a cuff (internal diameter 2.5 to 3.5 mm, Rusch AG, Waiblingen) into the trachea during inspiration.

To maintain anesthesia during the operation, the animals are given 2% propofol (Disoprivan 2%, Zeneca, Italy) i.v. in a dose of 12 to 14 ml/h via an infusion apparatus (Perfusor®, ED1-300, B. Braun, Melsungen AG). As analgesic the rabbits are given fentanyl (Fentanyl-Janssen 0.5 mg, Janssen-Cilag GmbH, Neuss) in a dose of 0.01 mg/kg i.v.

immediately after intubation and then as required during the operation, roughly every 30 minutes, to maintain the surgical tolerance stage.

Using a small-animal ventilator (Anesthesia Workstation, Hallowell EMC, Völker GmbH, Kaltenkirchen), the rabbits are ventilated with 100% oxygen at a breathing pressure of about 10 mm Hg, a respiratory volume of 8 to 12 ml/kg body weight and a respiratory rate of 29 to 32 breaths per minute, giving a $CO_2$ partial pressure of about 35 mm Hg in the expired air. Cardiovascular function is monitored intraoperatively via an ECG (Medtronic®, 9790 Programmer, Vitatron Medical B. V., Dieren, Netherlands). Respiration and circulation are monitored by pulse oximetry and capnometry.

Aortic Cross-Clamping:

Preparation of the right common carotid artery. Introduction of a polyurethane catheter (Cavafix®, 1.1*1.7 mm/16 G, ref. 4173589, B. Braun Melsungen AG, Melsungen, Germany) into the artery. After cannulation of the right common carotid artery the chest is opened through the third intercostal space. The virus is introduced into the myocardium using the Sigscreen® method, ensuring that the infused vector remains in that location in particular. The thorax is then closed with ligatures (Nylon®, 2-0 USP) and sutured (Vicryl® (3-0) and Nylon® (3-0)).

Analgesia: The animals receive carprofen (Rimadyl®, Pfizer, 4 mg/kg every 12 hours) and buprenorphine (Temgesic®, Boehringer, 0.01 mg/kg every 12 hours) for 72 hours after the operation.

Euthanasia of the Animals:

On the last day of the study the animals undergo general anesthesia as described in Section 4. Euthanasia takes place in deep narcosis induced by pentobarbital 0.48 g/kg i.v. (Narcoren®, Rhone-Merieux GmbH, Laupheim).

Postmortem Macro Pathological Diagnosis and Sampling:

Immediately after death the heart is removed as quickly as possible by dividing the chest wall bilaterally at the level of the costal margin and completely disarticulating the sternum. The heart is separated from the afferent and efferent vessels and washed free of blood with cold sterile saline (isotonic sodium chloride solution, Delta-Pharm, Boehringer, Ingelheim) containing 5000 IU heparin. After gross pathological examination and weighing, the heart is preserved intact for further investigation. Hearts intended for single-cell isolation are briefly stored in a sterile tube of cold heparinized saline at about 4° C. pending immediate processing. For determination of GFP fluorescence, frozen sections are prepared. Freshly removed hearts intended for cell microscopy are similarly washed with sterile saline, dried with cellulose, and then deep-frozen in a test tube of liquid nitrogen (−196° C.) and stored at −80° C. until further processing. The animals are autopsied in accordance with veterinary college guidelines, paying particular attention to evaluation of the extent of typical heart failure symptoms: ascites, pleural effusion, heart weight, heart shape, liver congestion and liver weight.

Disposal of the Carcasses:

After collection in a deep-freeze cabinet at −20° C., the carcasses are fetched by the carcass disposal unit for disposal.

Construction and Purification of Recombinant Adenovirus:

A human EDG2 receptor was cloned by using a PCR-based strategy on the basis of the coding sequence of the human EDG2 receptor. Recombinant (E1/E3-deficient) flag-tagged adenoviruses for this receptor (Ad-EDG2-GFP) were generated, expressing the transgene and green fluorescence protein (GFP) under control of two independent CMV promoters. As a control, Ad-GFP without further transgenes was used. Large virus stocks were prepared and adenoviral titers were determined using plaque titration and GFP expression titration in non E1-expressing cells.

Cloning of EDG2:

The DNA of the EDG2 receptor was amplified from cDNA from human brain by PCR using the forward primer 5'-gcggggggtaccaccatggctgccatctctacttccatcc-3' (SEQ ID NO. 6) and the reverse primer 5'-gcggggctcgagtcacttgtcgtcgtcgtcctatagtcaaccacaga gtgatcattgct-3' (SEQ ID NO. 7).

The PCR reaction was performed at 58° C. annealing for 1 min and 72° C. amplification temperature for 1 min over 20 cycles with the Expand High Fidelity PCR System (Roche Molecular Biochemicals, Mannheim, Germany). Within the PCR reaction, a HA-tag Epitope of 9 amino acids from hemaglutinin of the human influenza A virus) was generated in-frame at the 3'-end of the gene.

The PCR fragment was cloned into the plasmid pAd-Shuttle (Q Biogene, Heidelberg, Germany) by using the restriction sites for KpnI and XhoI and the sequence of resulting pAd Track-CMV-EDG2 was checked by sequencing (MediGenomix, Martinsried, Germany).

SEQ ID NO. 1 discloses the polynucleotide sequence of EDG2 comprising the coding region of an HA-tag within the 30 nucleotides of the 3'-end.

SEQ ID NO. 2 refers to the amino acid sequence of EDG2 comprising the 9 amino acid HA-tag of the C-terminus.

In SEQ ID NO. 8 the polynucleotide sequence of EDG2 having a 5'-HindIII and 3'XhoI site is disclosed. This EDG2 gene has been cloned into HindIII/XbaI sites of pcDNA 3.1 (invitrogen). Such a vector construct is also suitable for amplifying the EDG2 gene.

Construction of Recombinant Flag-Tagged Adenovirus (pAD easy 1-EDG2-HA-GFP):

The plasmid pADTrack CMV-EDG2 c-HA was linearized with PmeI (New England Biolabs, Beverly, Mass.) overnight, dephosphorylated and purified (GFX DNA and Gel Purification Kit; Amersham Pharmacia Biotech, Uppsala, Sweden). For homologous recombination, electro competent E. coli BJ5183 (Stratagene, La Jolla, Calif.) were cotransformed with 1 µg of the linearized plasmid pADTrack CMV EDG2 c-HA and 0.1 µg pAdeasyl at 2500 V, 200 W and 25 µFD (E. coli-pulser; Biorad, Heidelberg, Germany), plated and incubated overnight at 37° C. The resulting vector, pAdEasyl-edg2-cHA-GFP, contained the full recombinant adenoviral DNA for Transfection. The full DNA sequence is shown in SEQ ID NO. 5.

The colonies were checked after minipreparation of the plasmid DNA with PacI and the positive clones were retransformed into E. coli DH5a.

For transfection (Effectene Transfection reagent; Qiagen, Hilden, Germany) of 293 cells, plasmid DNA was digested with PacI. The cells were cultured for 7 days and harvested by scraping and centrifugation. The pellet was resuspended in Dulbecco's PBS and the cells were lysed by four repetitive freezing (−80° C.) and thawing (37° C.) cycles. Cell debris was removed by centrifugation and the lysate stored at −80° C.

For plaque selection of recombinant virus, 293 cells were infected in Dulbecco's PBS for 1 hour at room temperature under gentle agitation with different serial dilutions of lysate from transfection. Following the infection, the cells were overlayed with growth medium containing 0.5% agarose (1:1 mix of modified Eagles medium 2×, Gibco Life technologies #21935, supplemented with 20% Serum, 2× penicillin/streptomycin, 2× L-glutamin and agarose in water 1%, Seacam). 5–14 days post infection the cell layer was monitored for formation of plaques which were picked using a pasteur pipette, resuspended in 0.5 ml Dulbeccos PBS and stored at −80° C. The plaques were used for further amplification rounds on 293 cells.

Model of Heart Failure:

New Zealand White rabbits were treated by rapid pacing at 360 beats/min after pacemaker implantation. Under this protocol, a tachycardia-induced heart failure (HF) develops reproducibly over two weeks. The average +dp/dtmax-value in failing hearts was 2200±320 mmHg/sec (vs. 3200±390 mmHg/sec in healthy controls; $p<0.05$), and LVEDP increased from 3.6±0.4 mmHg to 13±3.4 ($p<0.05$).

Adenoviral Gene Transfer to Rabbit Myocardium:

Before the start of rapid pacing, all rabbits received catheter-based adenoviral gene transfer ($4×10^{10}$ pfu) to the myocardium. For the intervention, the rabbits were anesthetized with fentanyl and propofol. The efficacy of gene transfer was assessed in all hearts after the end of the experiments by investigating transverse freeze-cut sections for expression of GFP by fluorescence microscopy. Morphological changes were assessed after fixation with 4% paraformaldehyde. Gene transfer led to reproducible transgene expression in ~50% of cardiomyocytes.

Shortening Measurements in Isolated Cardiomyocytes:

Contractility of infected cardiomyocytes was measured by an electro-optical monitoring system connected to online digitalized assessment of amplitude and velocity of shortening and of relaxation. Transgene-positive cardiomyocytes were identified by co-expression of GFP under fluorescent light. After the contraction amplitude reached stability, increasing concentrations of isoproterenol were applied at constant concentrations of lysophosphatidic acid (LPA; $10^{-5}$ mol/l); or increasing LPA concentrations were added to constant concentrations of isoproterenol ($10^{-8}$ mol/l).

Figure 2:
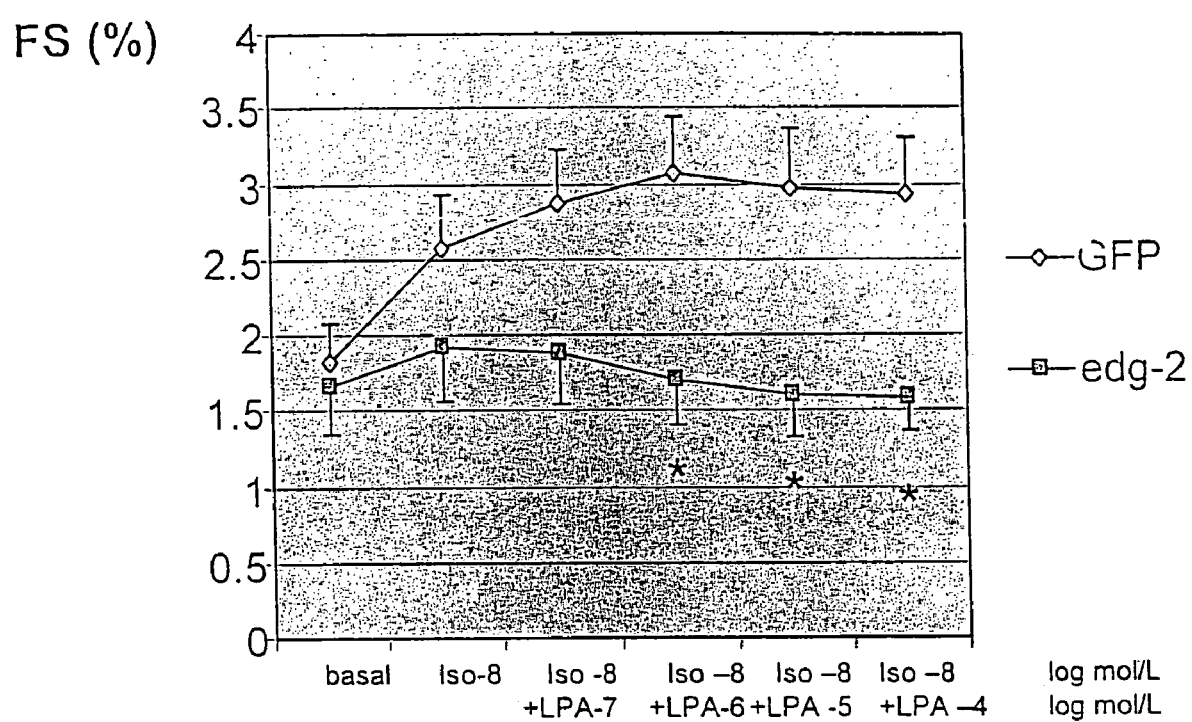
FIG. 2:
Contraction amplitude of single cardiomyocytes isolated from failing hearts. Similar to the experiments shown in FIG. 1, FS was compared in cardiomyocytes after gene transfer with either Ad-GFP or Ad-EDG2-GFP in vitro. Fractional shortening was determined in response to increasing LPA concentrations after prestimulation with 10 µM of isoproterenol. Data represent means±SEM.

Single Cell Contraction:

In order to investigate the effects of EDG2 on cardiomyocyte contractility, fractional shortening and velocity of shortening in single, isolated cardiomyocytes from failing hearts after ex vivo gene transfer was measured. At a concentration of lysophosphatidic acid (LPA) of $10^{-5}$ mol/l which does not alter basal contractility, increasing concentrations of isoproterenol had a significantly lower positively inotropic effect in EDG2-overexpressing cardiomyocytes (FIG. 1). After prestimulation with a low concentration of isoproterenol ($10^{-8}$ mol/l), increasing concentrations of LPA showed a significant negatively inotropic effect in EDG2-overexpressing cardiomyocytes whereas no effect was observed in the control GFP group (FIG. 2). In the absence of prestimulation with isoproterenol, LPA has no effect on the contractility of cardiomyocytes.

Western Blot of Infected Cardiomyocytes:

Cardiomyocytes were harvested 48 hours after adenoviral infection. The cells were homogenized and cytosolic extracts were then used for western blotting with antibodies against the HA tag or against EDG2. Horse radish peroxidase-coupled goat anti-rabbit antibodies by Dianova, Germany, were used as second antibodies.

In Vivo Adenoviral Delivery of Transgene to Failing Heart:

Overexpression of all transgenes was investigated by studying the co-expression of GFP in the hearts after in vivo gene transfer, since all transgenes were expressed together with GFP. A macroscopic slice of a rabbit heart infected with Ad-EDG 2-GFP showed GFP co-expression occurring throughout the left ventricle when determined by anti-GFP antibody staining.

Transgene Expression Assessed by Western Blotting:

Western blotting documented the expression of EDG2 by means of an antibody directed against the HA tag or by a specific antibody against EDG2 in cardiomyocytes.

Preparation and Culture of Adult Ventricular Cardiomyocytes and Adenovirus Infections:

Single calcium-tolerant ventricular cardiomyocytes were isolated from failing White New Zealand rabbit hearts. Briefly, the hearts were perfused and digested with collagenase. The isolated cardiomyocytes were cultured in modified M199 on laminin-precoated dishes (5–10 µg/cm$^2$) at a density of $1.5×10^5$ cells per cm$^2$ (at 5% CO$_2$ and 37° C.). For contraction experiments, the cells were infected with adenovirus (multiplicity of infection (moi) 1 pfu/cell) 5 hours after plating. 50–60% of the infected cardiomyocytes expressed the transgene at this titer.

Myocardial Contractility Measurement by Echocardiography and Intraventricular Tip Catheter:

Left ventricular contractility was examined by echocardiography before the initiation of rapid pacing, after 1 week and after two weeks after the start of pacing. Tip catheter measurements were performed after 2 weeks of pacing. The rabbits were anesthetized; ECG was monitored continuously.

For echocardiography, a 7.5 MHz probe was fixed on a tripod. Standard sections were recorded, which were well reproducible. For tip catheter measurements, a Millar 3F tip catheter connected to a differentiating device was placed in the left ventricle via a sheath placed in the carotid artery. After definition of basal contractility and left ventricular pressure, 200 µL of NaCl (0.9%) was injected as a negative control. Isoproterenol and lysophosphatidic acid (LPA) were infused intravenously at increasing doses. After a 20 min equilibration period, tip catheter measurements were carried out.

Figure 3:
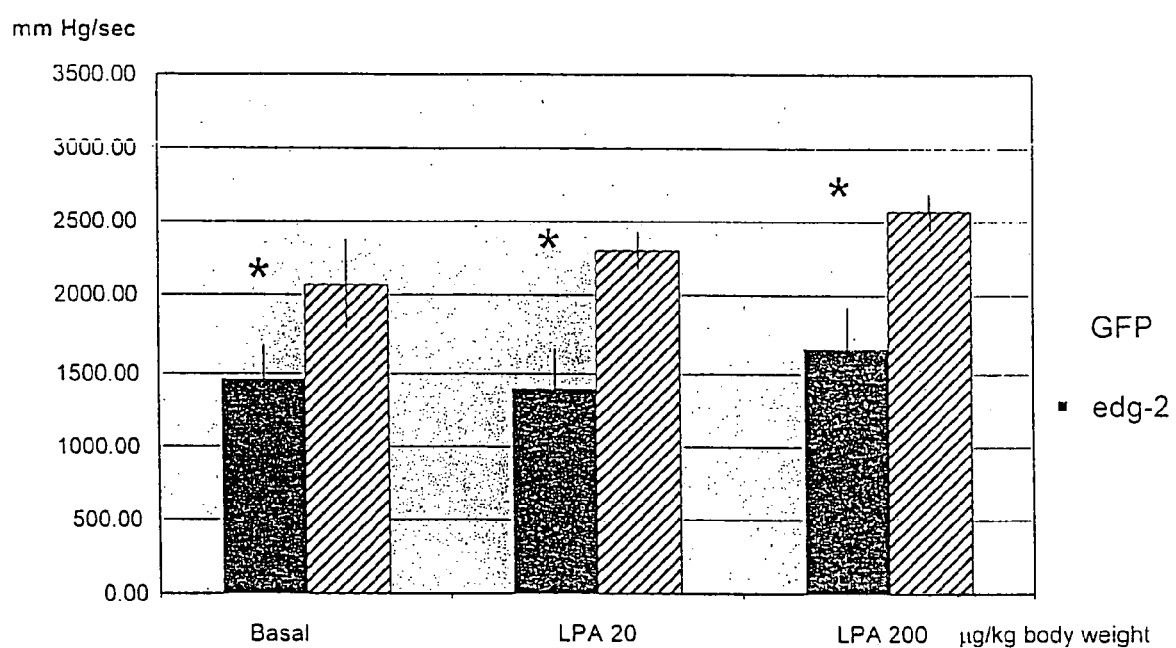
FIG. 3:
Maximum first derivative of left ventricular pressure (LV dp/dt max) at baseline and in response to increasing doses of LPA as determined by tip catheterization. In rabbits with terminal heart failure due to rapid pacing and after two weeks after gene transfer of either GFP or EDG2. Data represent means±SEM. All measurements were done in 8 animals in triplicates *$p<0.05$ vs GFP.
Figure 4:
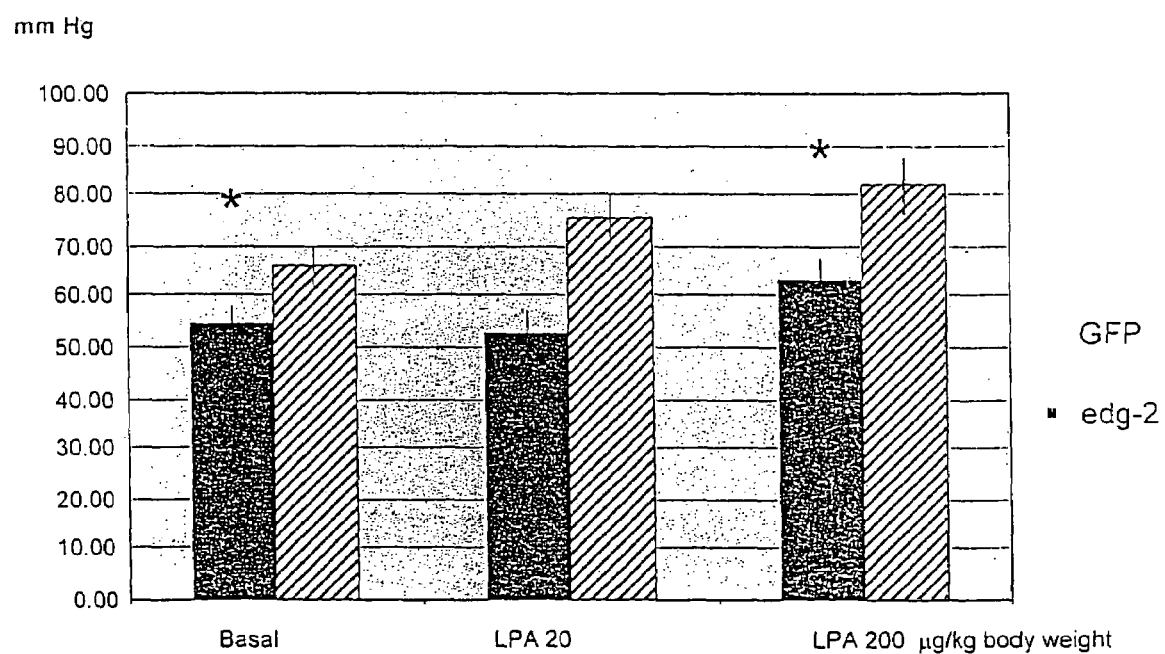
FIG. 4:
Left ventricular systolic pressure at baseline and in response to increasing doses of LPA as determined by tip catheterization in rabbits with terminal heart failure due to rapid pacing and after two weeks after gene transfer of either GFP or EDG2. Data represent means±SEM. All measurements were done in 8 animals in triplicates. *$p<0.05$ vs GFP.

Deterioration of LV Dysfunction in Pacing-Induced Heart Failure:

FIG. 3 shows tip catheterization measurements after 2 weeks of rapid pacing in rabbits suffering from severe heart failure (NYHA IV). In the EDG2-expression group, the first derivatives of LV pressure (dp/dt max) were significantly lower than in the Ad-GFP-infected control group at basal conditions and at increasing doses of LPA. This was also true for the increases in systolic LV pressure (FIG. 4).

Echocardiography showed a marked hypertrophy of the myocardium after 2 weeks in the EDG2-overexpressing hearts, which was also evidenced by decreases in systolic and diastolic diameters. The mean thicknesses of the posterior wall and of the septum of the LV were significantly greater in EDG2-overexpressing hearts compared to the GFP controls. The time course of LV fractional shortening (FS) was assessed by serial echocardiography during the two week-observation period. In both groups, FS declined gradually during the time period of rapid pacing.

The invention claimed is:

1. A myocardial cell of a non-human mammal, wherein the myocardial cell contains an adenoviral vector sequence for simultaneous expression of G protein coupled receptor EDG002 and a cellular marker.

2. The myocardial cell of claim 1, wherein the cellular marker is a fluorescent protein.

3. The myocardial cell of claim 2, wherein the cellular marker is Green Fluorescent Protein.

4. The myocardial cell of claim 2, wherein the adenoviral vector sequence comprises of a recombinant E1/E3 deficient adenovirus which expresses the G protein coupled receptor EDG2 and the fluorescent protein under control of two independent promoters.

5. The myocardial cell of claim 4 wherein the two independent Promoters are two CMV promoters.

6. A method of producing of a myocardial cell according to claim 1, comprising:
 a. removing the heart of a non-human mammal,
 b. perfusing the removed heart, digesting the removed heart whit collagenase, and isolating cardiomyocytes, and
 c infecting the isolated cardiomyocytes with an adenoviral vector comprising a recombinant E1/E3 deficient adenovirus which expresses the G protein coupled receptor EDG2 and a cellular marker under control of two independent promoters.

7. The method of claim 6, wherein the cellular marker is a fluorescent protein.

* * * * *

SEQUENCE LISTING

<160> NUMBER OF SEQ ID NOS: 8

<210> SEQ ID NO 1
<211> LENGTH: 1122
<212> TYPE: DNA
<213> ORGANISM: Homo sapiens

<400> SEQUENCE: 1

```
atggctgcca tctctacttc catccctgta atttcacagc cccagttcac agccatgaat     60
gaaccacagt gcttctacaa cgagtccatt gccttctttt ataaccgaag tggaaagcat    120
cttgccacag aatggaacac agtcagcaag ctggtgatgg gacttggaat cactgtttgt    180
atcttcatca tgttggccaa cctattggtc atggtggcaa tctatgtcaa ccgccgcttc    240
cattttccta tttattacct aatggctaat ctggctgctg cagacttctt tgctgggttg    300
gcctacttct atctcatgtt caacacagga cccaatactc ggagactgac tgttagcaca    360
tggctccttc gtcagggcct cattgacacc agcctgacgg catctgtggc caacttactg    420
gctattgcaa tcgagaggca cattacggtt ttccgcatgc agctccacac acggatgagc    480
aaccggcggg tagtggtggt cattgtggtc atctggacta tggccatcgt tatgggtgct    540
atacccagtg tgggctggaa ctgtatctgt gatattgaaa attgttccaa catggcaccc    600
ctctacagtg actcttactt agtcttctgg gccattttca acttggtgac ctttgtggta    660
atggtggttc tctatgctca catctttggc tatgttcgcc agaggactat gagaatgtct    720
cggcatagtt ctggaccccg gcggaatcgg gataccatga tgagtcttct gaagactgtg    780
gtcattgtgc ttggggcctt tatcatctgc tggactcctg gattggtttt gttacttcta    840
gacgtgtgct gtccacagtg cgacgtgctg gcctatgaga aattcttcct tctccttgct    900
gaattcaact ctgccatgaa ccccatcatt tactcctacc gcgacaaaga aatgagcgcc    960
acctttaggc agatcctctg ctgccagcgc agtgagaacc ccaccggccc cacagaaggc   1020
tcagaccgct cggcttcctc cctcaaccac accatcttgg ctggagttca cagcaatgat   1080
cactctgtgg tttatcccta tgacgtcccc gactatgcct ga                       1122
```

<210> SEQ ID NO 2
<211> LENGTH: 373
<212> TYPE: PRT
<213> ORGANISM: Homo sapiens

<400> SEQUENCE: 2

```
Met Ala Ala Ile Ser Thr Ser Ile Pro Val Ile Ser Gln Pro Gln Phe
  1               5                  10                  15

Thr Ala Met Asn Glu Pro Gln Cys Phe Tyr Asn Glu Ser Ile Ala Phe
             20                  25                  30

Phe Tyr Asn Arg Ser Gly Lys His Leu Ala Thr Glu Trp Asn Thr Val
         35                  40                  45

Ser Lys Leu Val Met Gly Leu Gly Ile Thr Val Cys Ile Phe Ile Met
     50                  55                  60

Leu Ala Asn Leu Leu Val Met Val Ala Ile Tyr Val Asn Arg Arg Phe
 65                  70                  75                  80

His Phe Pro Ile Tyr Tyr Leu Met Ala Asn Leu Ala Ala Ala Asp Phe
                 85                  90                  95

Phe Ala Gly Leu Ala Tyr Phe Tyr Leu Met Phe Asn Thr Gly Pro Asn
            100                 105                 110
```

-continued

```
            Thr Arg Arg Leu Thr Val Ser Thr Trp Leu Leu Arg Gln Gly Leu Ile
                115                 120                 125

Asp Thr Ser Leu Thr Ala Ser Val Ala Asn Leu Leu Ala Ile Ala Ile
            130                 135                 140

Glu Arg His Ile Thr Val Phe Arg Met Gln Leu His Thr Arg Met Ser
    145                 150                 155                 160

Asn Arg Arg Val Val Val Ile Val Ile Trp Thr Met Ala Ile
                        165                 170                 175

Val Met Gly Ala Ile Pro Ser Val Gly Trp Asn Cys Ile Cys Asp Ile
                    180                 185                 190

Glu Asn Cys Ser Asn Met Ala Pro Leu Tyr Ser Asp Ser Tyr Leu Val
                    195                 200                 205

Phe Trp Ala Ile Phe Asn Leu Val Thr Phe Val Met Val Val Leu
                    210                 215                 220

Tyr Ala His Ile Phe Gly Tyr Val Arg Gln Arg Thr Met Arg Met Ser
    225                 230                 235                 240

Arg His Ser Ser Gly Pro Arg Arg Asn Arg Asp Thr Met Met Ser Leu
                        245                 250                 255

Leu Lys Thr Val Val Ile Val Leu Gly Ala Phe Ile Ile Cys Trp Thr
                    260                 265                 270

Pro Gly Leu Val Leu Leu Leu Asp Val Cys Cys Pro Gln Cys Asp
                    275                 280                 285

Val Leu Ala Tyr Glu Lys Phe Phe Leu Leu Leu Ala Glu Phe Asn Ser
                    290                 295                 300

Ala Met Asn Pro Ile Ile Tyr Ser Tyr Arg Asp Lys Glu Met Ser Ala
    305                 310                 315                 320

Thr Phe Arg Gln Ile Leu Cys Cys Gln Arg Ser Glu Asn Pro Thr Gly
                        325                 330                 335

Pro Thr Glu Gly Ser Asp Arg Ser Ala Ser Ser Leu Asn His Thr Ile
                    340                 345                 350

Leu Ala Gly Val His Ser Asn Asp His Ser Val Val Tyr Pro Tyr Asp
                    355                 360                 365

Val Pro Asp Tyr Ala
            370

<210> SEQ ID NO 3
<211> LENGTH: 798
<212> TYPE: DNA
<213> ORGANISM: Aequorea victoria

<400> SEQUENCE: 3
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctgggcac    420 aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
```

```
tacctgagca cccagtccgc cctgagcaaa gacccccaacg agaagcgcga tcacatggtc    660
ctgctggagt tcgtgaccgc cgccgggatc actctcggca tggacgagct gtacaagtcc    720
ggactcagat ctcgagctca agcttcgaat tctgcagtcg acggtaccgc gggcccggga    780
tccaccggat ctagataa                                                  798
```

```
<210> SEQ ID NO 4
<211> LENGTH: 265
<212> TYPE: PRT
<213> ORGANISM: Aequorea victoria

<400> SEQUENCE: 4
```

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Asp Gly Thr
                245                 250                 255

Ala Gly Pro Gly Ser Thr Gly Ser Arg
            260                 265
```

```
<210> SEQ ID NO 5
<211> LENGTH: 38306
<212> TYPE: DNA
<213> ORGANISM: adeno-associated virus 2
<220> FEATURE:
<223> OTHER INFORMATION: Vector
<220> FEATURE:
<223> OTHER INFORMATION: Adenoviral vector
<220> FEATURE:
<221> NAME/KEY: unsure
<222> LOCATION: 6..10
```

-continued

```
<223> OTHER INFORMATION: discrepancies in sequencing and/or publication
<220> FEATURE:
<221> NAME/KEY: unsure
<222> LOCATION: 29743..29745
<223> OTHER INFORMATION: discrepancies in sequencing and/or publication
<220> FEATURE:
<221> NAME/KEY: unsure
<222> LOCATION: 31494..31495
<223> OTHER INFORMATION: discrepancies in sequencing and/or publication
<220> FEATURE:
<221> NAME/KEY: unsure
<222> LOCATION: 31814..31816
<223> OTHER INFORMATION: discrepancies in sequencing and/or publication
<220> FEATURE:
<221> NAME/KEY: unsure
<222> LOCATION: 33405..33406
<223> OTHER INFORMATION: discrepancies in sequencing and/or publication
<220> FEATURE:
<221> NAME/KEY: unsure
<222> LOCATION: 33746..33748
<223> OTHER INFORMATION: discrepancies in sequencing and/or publication
<220> FEATURE:
<221> NAME/KEY: unsure
<222> LOCATION: 33757..33793
<223> OTHER INFORMATION: discrepancies in sequencing and/or publication
<220> FEATURE:
<221> NAME/KEY: unsure
<222> LOCATION: 35331..35336
<223> OTHER INFORMATION: discrepancies in sequencing and/or publication
<220> FEATURE:
<221> NAME/KEY: unsure
<222> LOCATION: 38295..38297
<223> OTHER INFORMATION: discrepancies in sequencing and/or publication

<400> SEQUENCE: 5
attaannnnn atcatcaata atatacctta ttttggattg aagccaatat gataatgagg      60
gggtggagtt tgtgacgtgg cgcggggcgt gggaacgggg cgggtgacgt aggttttagg     120
gcggagtaac ttgtatgtgt tgggaattgt agttttctta aaatgggaag ttacgtaacg     180
tgggaaaacg gaagtgacga tttgaggaag ttgtgggttt tttggctttc gtttctgggc     240
gtaggttcgc gtgcggtttt ctgggtgttt tttgtggact ttaaccgtta cgtcattttt     300
tagtcctata tatactcgct ctgcacttgg cccttttta cactgtgact gattgagctg      360
gtgccgtgtc gagtggtgtt tttttaatag gttttctttt ttactggtaa ggctgactgt     420
taggctgccg ctgtgaagcg ctgtatgttg ttctggagcg ggagggtgct attttgccta     480
ggcaggaggg ttttttcaggt gtttatgtgt ttttctctcc tattaatttt gttataccctc    540 ctatggggc tgtaatgttg tctctacgcc tgcgggtatg tattccccccg ggctatttcg     600 gtcgctttttt agcactgacc gatgaatcaa cctgatgtgt ttaccgagtc ttacattatg    660
actccggaca tgaccgagga gctgtcggtg gtgcttttta atcacggtga ccagttttt     720 tacggtcacg ccggcatggc cgtagtccgt cttatgctta taagggttgt ttttcctgtt    780
gtaagacagg cttctaatgt ttaaatgttt ttttgttatt ttattttgtg tttatgcaga    840
aacccgcaga catgtttgag agaaaaatgg tgtctttttc tgtggtggtt ccggagctta    900
cctgccttta tctgcatgag catgactacg atgtgctttc ttttttgcgc gaggctttgc    960 ctgattttt gagcagcacc ttgcatttta tatcgccgcc catgcaacaa agcttacatc    1020
ggggctacgc tggttagcat agctccgagt atgcgtgtca taatcagtgt gggttctttt    1080
gtcaaggttc ctggcgggga agtggccgcg ctggtccgtg cagacctgca cgattatgtt    1140
cagctggccc tgcgaaggga cctacgggat cgcggtattt ttgttaatgt tccgcttttg    1200
aatcttatac aggtctgtga ggaacctgaa ttttgcaat catgattcgc tgcttgaggc    1260
tgaaggtgga gggcgctctg gagcagattt ttacaatggc cggacttaat attcgggatt    1320
```

-continued

```
tgcttagaga tatattgaga aggtggcgag atgagaatta tttgggcatg gttgaaggtg    1380
ctggaatgtt tatagaggag attcaccctg aagggtttag cctttacgtc cacttggacg    1440
tgagggccgt ttgccttttg gaagccattg tgcaacatct tacaaatgcc attatctgtt    1500
ctttggctgt agagtttgac cacgccaccg gaggggagcg cgttcactta atagatcttc    1560
attttgaggt tttggataat cttttggaat aaaaaaaaaa acatggttct tccagctctt    1620
cccgctcctc ccgtgtgtga ctcgcagaac gaatgtgtag gttggctggg tgtggcttat    1680
tctgcggtgg tggatgttat cagggcagcg gcgcatgaag gagtttacat agaacccgaa    1740 gccaggggc gcctggatgc tttgagagag tggatatact acaactacta cacagagcga     1800
tctaagcggc gagaccggag acgcagatct gtttgtcacg cccgcacctg gttttgcttc    1860
aggaaatatg actacgtccg gcgttccatt tggcatgaca ctacgaccaa cacgatctcg    1920
gttgtctcgg cgcactccgt acagtaggga tcgtctacct ccttttgaga cagaaacccg    1980
cgctaccata ctggaggatc atccgctgct gcccgaatgt aacactttga caatgcacaa    2040
cgtgagttac gtgcgaggtc ttccctgcag tgtgggattt acgctgattc aggaatgggt    2100
tgttccctgg gatatggttc taacgcggga ggagcttgta atcctgagga agtgtatgca    2160
cgtgtgcctg tgttgtgcca acattgatat catgacgagc atgatgatcc atggttacga    2220
gtcctgggct ctccactgtc attgttccag tcccggttcc ctgcagtgta tagccggcgg    2280
gcaggttttg gccagctggt ttaggatggt ggtggatggc gccatgttta atcagaggtt    2340
tatatggtac cggaggtgg tgaattacaa catgccaaaa gaggtaatgt ttatgtccag     2400
cgtgtttatg aggggtcgcc acttaatcta cctgcgcttg tggtatgatg gccacgtggg    2460
ttctgtggtc cccgccatga gctttggata cagcgccttg cactgtggga ttttgaacaa    2520
tattgtggtg ctgtgctgca gttactgtgc tgatttaagt gagatcaggg tgcgctgctg    2580
tgcccggagg acaaggcgcc ttatgctgcg ggcggtgcga atcatcgctg aggagaccac    2640
tgccatgttg tattcctgca ggacggagcg gcggcggcag cagtttattc gcgcgctgct    2700
gcagcaccac cgcccctatcc tgatgcacga ttatgactct accccatgt aggcgtggac     2760 ttctccttcg ccgcccgtta agcaaccgca agttggacag cagcctgtgg ctcagcagct    2820
ggacagcgac atgaacttaa gtgagctgcc cgggagttt attaatatca ctgatgagcg     2880
tttggctcga caggaaaccg tgtggaatat aacacctaag aatatgtctg ttacccatga    2940
tatgatgctt tttaaggcca gccggggaga aggactgtg tactctgtgt gttgggaggg     3000
aggtggcagg ttgaatacta gggttctgtg agtttgatta aggtacggtg atctgtataa    3060
gctatgtggt ggtggggcta tactactgaa tgaaaaatga cttgaaattt tctgcaattg    3120
aaaaataaac acgttgaaac ataacacaaa cgattcttta ttcttgggca atgtatgaaa    3180
aagtgtaaga ggatgtggca atatttcat taatgtagtt gtggccagac cagtcccatg      3240
aaaatgacat agagtatgca cttggagttg tgtctcctgt ttcctgtgta ccgtttagtg    3300
taatggttag tgttacaggt ttagttttgt ctccgtttaa gtaaacttga ctgacaatgt    3360
tacttttggc agttttaccg tgagattttg gataagctga taggttaggc ataaatccaa    3420
cagcgtttgt ataggctgtg ccttcagtaa gatctccatt tctaaagttc caatattctg    3480
ggtccaggaa ggaattgttt agtagcactc catttttcgtc aaatcttata ataagatgag   3540
cactttgaac tgttccagat attggagcca aactgccttt aacagccaaa actgaaactg    3600
tagcaagtat ttgactgcca catttttgtta agaccaaagt gagtttagca tctttctctg   3660
```

-continued

```
catttagtct acagttagga gatggagctg gtgtggtcca caaagttagc ttatcattat      3720
ttttgtttcc tactgtaatg gcacctgtgc tgtcaaaact aaggccagtt cctagtttag      3780
gaaccatagc cttgtttgaa tcaaattcta ggccatggcc aattttttgtt ttgaggggat     3840
ttgtgtttgg tgcattaggt gaaccaaatt caagcccatc tcctgcatta atggctatgg     3900
ctgtagcgtc aaacatcaac cccttggcag tgcttaggtt aacctcaagc ttttttggaat    3960
tgtttgaagc tgtaaacaag taaaggcctt tgttgtagtt aatatccaag ttgtgggctg     4020
agtttataaa aagagggccc tgtcctagtc ttagatttag ttggttttga gcatcaaacg     4080
gataactaac atcaagtata aggcgtctgt tttgagaatc aatccttagt cctcctgcta     4140
cattaagttg catattgcct tgtgaatcaa acccaaggc tccagtaact ttagtttgca      4200
aggaagtatt attaatagtc acacctggac cagttgctac ggtcaaagtg tttaggtcgt     4260
ctgttacatg caaaggagcc ccgtacttta gtcctagttt tccattttgt gtataaatgg     4320
gctctttcaa gtcaatgccc aagctaccag tggcagtagt tagaggggggt gaggcagtga    4380
tagtaagggt actgctatcg gtggtggtga gggggcctga tgtttgcagg gctagctttc     4440
cttctgacac tgtgagggt ccttgggtgg caatgctaag tttggagtcg tgcacggtta      4500
gcggggcctg tgattgcatg gtgagtgtgt tgcccgcgac cattagaggt gcggcggcag     4560
ccacagttag ggcttctgag gtaactgtga ggggtgcaga tatttccagg tttatgtttg     4620
acttggtttt tttgagaggt gggctcacag tggttacatt ttgggaggta aggttgccgg     4680
cctcgtccag agagaggccg ttgcccattt tgagcgcaag catgccattg gaggtaacta     4740
gaggttcgga taggcgcaaa gagagtaccc caggggggact ctcttgaaac ccattggggg   4800
atacaaaggg aggagtaaga aaaggcacag ttggaggacc ggtttccgtg tcatatggat     4860
acacggggtt gaaggtatct tcagacggtc ttgcgcgctt catctgcaac aacatgaaga    4920
tagtgggtgc ggatggacag gaacaggagg aaactgacat tccatttaga ttgtggagaa    4980
agtttgcagc caggaggaag ctgcaataacc agagctggga ggagggcaag gaggtgctgc    5040
tgaataaact ggacagaaat ttgctaactg attttaagta agtgatgctt tattatttttt    5100
ttttattagt taaagggaat aagatccccg ggtactctag ttataactag aggatcttga     5160
tgtaatccaa ggttaggaca gttgcaaatc acagtgagaa cacagggtcc cctgtcccgc    5220
tcaactagca gggggcgctg gtaaactcc cgaatcaggc tacgggcaag ctctccctgg     5280
gcggtaagcc ggacgccgtg cgccgggccc tcgatatgat cctcgggcaa ttcaaagtag     5340
caaaactcac cggagtcgcg ggcaaagcac ttgtggcggc gacagtggac caggtgtttc     5400
aggcgcagtt gctctgcctc tccacttaac attcagtcgt agccgtccgc cgagtccttt     5460
accgcgtcaa agttaggaat aaattgatcc ggatagtggc cggagggtcc cgagaagggg    5520
ttaaagtaga ccgatggcac aaactcctca ataaattgca gagttccaat gcctccagag    5580
cgcggctcag aggacgaggt ctgcagagtt aggattgcct gacgaggcgt gaatgaagga    5640
cggccggcgc cgccgatctg aaatgtcccg tccggacgga gaccaagcga ggagctcacc    5700
gactcgtcgt tgagctgaat acctcgccct ctgattgtca ggtgagttat accctgcccg    5760
ggcgaccgca ccctgtgacg aaagccgccc gcaagctgcg cccctgagtt agtcatctga    5820
acttcggcct gggcgtctct gggaagtacc acagtggtgg gagcgggact ttcctggtac     5880
accagggcag cgggccaact acggggatta aggttattac gaggtgtggt ggtaatagcc    5940
gcctgttcca agagaattcg gtttcggtgg gcgcggattc cgttgacccg ggatatcatg    6000
tggggtcccg cgctcatgta gtttattcgg gttgagtagt cttgggcagc tccagccgca    6060
```

-continued

```
agtcccattt gtggctggta actccacatg tagggcgtgg gaatttcctt gctcataatg   6120
gcgctgacga caggtgctgg cgccgggtgt ggccgctgga gatgacgtag ttttcgcgct   6180
taaatttgag aaagggcgcg aaactagtcc ttaagagtca gcgcgcagta tttactgaag   6240
agagcctccg cgtcttccag cgtgcgccga agctgatctt cgcttttgtg atacaggcag   6300 ctgcggtga gggatcgcag agacctgttt tttattttca gctcttgttc ttggcccctg   6360
ctctgttgaa atatagcata cagagtggga aaatcctgt ttctaagctc gcgggtcgat   6420 acggttcgt tgggcgccag acgcagcgct cctcctcctg ctgctgccgc cgctgtggat   6480
ttcttgggct ttgtcagagt cttgctatcc ggtcgccttt gcttctgtgt ggccgctgct   6540
gttgctgccg ctgccgctgc cgccggtgca gtatgggctg tagagatgac ggtagtaatg   6600
caggatgtta cggggaagg ccacgccgtg atggtagaga agaaagcggc gggcgaagga   6660
gatgttgccc ccacagtctt gcaagcaagc aactatggcg ttcttgtgcc cgcgccatga   6720
gcggtagcct tggcgctgtt gttgctcttg ggctaacggc ggcggctgct tggacttacc   6780
ggccctggtt ccagtggtgt cccatctacg gttgggtcgg cgaacgggca gtgccggcgg   6840
cgcctgagga gcggaggttg tagccatgct ggaaccggtt gccgatttct ggggcgccgg   6900 cgagggaat gcgaccgagg gtgacggtgt ttcgtctgac acctcttcga cctcggaagc   6960
ttcctcgtct aggctctccc agtcttccat catgtcctcc tcctcctcgt ccaaaacctc   7020
ctctgcctga ctgtcccagt attcctcctc gtccgtgggt ggcggcggca gctgcagctt   7080 cttttttgggt gccatcctgg gaagcaaggg cccgcggctg ctgctgatag ggctgcggcg   7140 gcgggggat tgggttgagc tcctcgccgg actggggtc caagtaaacc ccccgtccct   7200
ttcgtagcag aaactcttgg cgggctttgt tgatggcttg caattggcca agaatgtggc   7260
cctgggtaat gacgcaggcg gtaagctccg catttggcgg gcgggattgg tcttcgtaga   7320
acctaatctc gtgggcgtgg tagtcctcag gtacaaattt gcgaaggtaa gccgacgtcc   7380
acagccccgg agtgagtttc aaccccggag ccgcggactt ttcgtcaggc gagggaccct   7440
gcagctcaaa ggtaccgata atttgacttt cgttaagcag ctgcgaattg caaaccaggg   7500
agcggtgcgg ggtgcatagg ttgcagcgac agtgacactc cagtagaccg tcaccgctca   7560
cgtcttccat tatgtcagag tggtaggcaa ggtagttggc tagctgcaga aggtagcagt   7620
ggccccaaag cggcggaggg cattcgcggt acttaatggg cacaaagtcg ctaggaagtg   7680
cacagcaggt ggcgggcaag attcctgagc gctctaggat aaagttccta aagttctgca   7740
acatgctttg actggtgaag tctggcagac cctgttgcag ggttttaagc aggcgttcgg   7800
ggaaaatgat gtccgccagg tgcgcggcca cggagcgctc gttgaaggcc gtccataggt   7860
ccttcaagtt ttgctttagc agtttctgca gctccttgag gttgcactcc tccaagcact   7920
gctgccaaac gcccatggcc gtctgccagg tgtagcatag aaataagtaa acgcagtcgc   7980
ggacgtagtc gcggcgcgcc tcgcccttga gcgtggaatg aagcacgttt tgcccaaggc   8040
ggttttcgtg caaaattcca aggtaggaga ccaggttgca gagctccacg ttggagatct   8100
tgcaggcctg gcgtacgtag ccctgtcgaa aggtgtagtg caatgtttcc tctagcttgc   8160
gctgcatctc cgggtcagca aagaaccgct gcatgcactc aagctccacg gtaacgagca   8220
ctgcggccat cattagtttg cgtcgctcct ccaagtcggc aggctcgcgc gtttgaagcc   8280
agcgcgctag ctgctcgtcg ccaactgcgg gtaggccctc ctctgtttgt tcttgcaaat   8340
ttgcatccct ctccaggggc tgcgcacggc gcacgatcag ctcactcatg actgtgctca   8400
```

-continued

```
tgaccttggg gggtaggtta agtgccgggt aggcaaagtg ggtgacctcg atgctgcgtt    8460
ttagtacggc taggcgcgcg ttgtcaccct cgagttccac caacactcca gagtgacttt    8520
catttttcgct gttttcctgt tgcagagcgt ttgccgcgcg cttctcgtcg cgtccaagac   8580
cctcaaagat ttttggcact tcgttgagcg aggcgatatc aggtatgaca gcgccctgcc    8640
gcaaggccag ctgcttgtcc gctcggctgc ggttggcacg gcaggatagg ggtatcttgc    8700
agttttggaa aaagatgtga taggtggcaa gcacctctgg cacggcaaat acggggtaga    8760
agttgaggcg cgggttgggc tcgcatgtgc cgttttcttg gcgtttgggg ggtacgcgcg    8820
gtgagaatag gtggcgttcg taggcaaggc tgacatccgc tatggcgagg ggcacatcgc    8880
tgcgctcttg caacgcgtcg cagataatgg cgcactggcg ctgcagatgc ttcaacagca    8940
cgtcgtctcc cacatctagg tagtcgccat gcctttcgtc cccccgcccg acttgttcct    9000
cgtttgcctc tgcgttgtcc tggtcttgct ttttatcctc tgttggtact gagcggtcct    9060
cgtcgtcttc gcttacaaaa cctgggtcct gctcgataat cacttcctcc tcctcaagcg    9120
ggggtgcctc gacggggaag gtggtaggcg cgttggcggc atcggtggag gcggtggtgg    9180
cgaactcaga gggggcggtt aggctgtcct tcttctcgac tgactccatg atcttttttct   9240
gcctatagga gaaggaaatg gccagtcggg aagaggagca gcgcgaaacc accccccgagc   9300
gcggacgcgg tgcggcgcga cgtcccccaa ccatggagga cgtgtcgtcc ccgtccccgt    9360
cgccgccgcc tccccgggcg cccccaaaaa agcggatgag gcggcgtatc gagtccgagg    9420
acgaggaaga ctcatcacaa gacgcgctgg tgccgcgcac acccagcccg cggccatcga    9480
cctcggcggc ggatttggcc attgcgccca agaagaaaaa gaagcgccct tctcccaagc    9540
ccgagcgccc gccatcacca gaggtaatcg tggacagcga ggaagaaaga gaagatgtgg    9600
cgctacaaat ggtgggtttc agcaacccac cggtgctaat caagcatggc aaaggaggta    9660
agcgcacagt gcggcggctg aatgaagacg acccagtggc gcgtggtatg cggacgcaag    9720
aggaagagga agagcccagc gaagcggaaa gtgaaattac ggtgatgaac ccgctgagtg    9780
tgccgatcgt gtctgcgtgg gagaagggca tggaggctgc gcgcgcgctg atggacaagt    9840
accacgtgga taacgatcta aaggcgaact tcaaactact gcctgaccaa gtggaagctc    9900
tggcggccgt atgcaagacc tggctgaacg aggagcaccg cgggttgcag ctgaccttca    9960
ccagcaacaa gaccttttgtg acgatgatgg ggcgattcct gcaggcgtac ctgcagtcgt   10020
ttgcagaggt gacctacaag catcacgagc ccacgggctg cgcgttgtgg ctgcaccgct    10080
gcgctgagat cgaaggcgag cttaagtgtc tacacggaag cattatgata aataaggagc    10140
acgtgattga aatggatgtg acgagcgaaa acgggcagcg cgcgctgaag gagcagtcta    10200
gcaaggccaa gatcgtgaag aaccgtgggg ccgaaatgt ggtgcagatc tccaacaccg    10260
acgcaaggtg ctgcgtgcac gacgcggcct gtccggccaa tcagttttcc ggcaagtctt    10320
gcggcatgtt cttctctgaa ggcgcaaagg ctcagtggc ttttaagcag atcaaggctt    10380
ttatgcaggc gctgtatcct aacgcccaga ccgggcacgg tcacctttg atgccactac    10440
ggtgcgagtg caactcaaag cctgggcacg cgccctttttt gggaaggcag ctaccaaagt    10500
tgactccgtt cgccctgagc aacgcggagg acctggacgc ggatctgatc tccgacaaga    10560
gcgtgctggc cagcgtgcac cacccggcgc tgatagtgtt ccagtgctgc aaccctgtgt    10620
atcgcaactc gcgcgcgcag ggcggaggcc ccaactgcga cttcaagata tcggcgcccg    10680
acctgctaaa cgcgttggtg atggtgcgca ggcctgtggag tgaaaacttc accgagctgc    10740
cgcggatggt tgtgcctgag tttaagtgga gcactaaaca ccagtatcgc aacgtgtccc    10800
```

-continued

```
tgccagtggc gcatagcgat gcgcggcaga acccctttga tttttaaacg gcgcagacgg   10860
caagggtggg ggtaaataat cacccgagag tgtacaaata aaagcatttg cctttattga   10920
aagtgtctct agtacattat ttttacatgt ttttcaagtg acaaaaagaa gtggcgctcc   10980
taatctgcgc actgtggctg cggaagtagg gcgagtggcg ctccaggaag ctgtagagct   11040
gttcctggtt gcgacgcagg gtgggctgta cctggggact gttgagcatg gagttgggta   11100
ccccggtaat aaggttcatg gtgggggttgt gatccatggg agtttggggc cagttggcaa   11160
aggcgtggag aaacatgcag cagaatagtc cacaggcggc cgagttgggc ccctgtacgc   11220
tttgggtgga cttttccagc gttatacagc ggtcggggga agaagcaatg gcgctacggc   11280
gcaggagtga ctcgtactca aactggtaaa cctgcttgag tcgctggtca gaaaagccaa   11340
agggctcaaa gaggtagcat gcgggttcca ggcaaaggcc atccagtgta cgccccagt    11400 ctcgcgaccg gccgtattga ctatggcgca ggcgagcttg tgtggagaaa caaagcctgg   11460
aaagcgcttg tcataggtgc ccaaaaaata tggcccacaa ccaagatctt tgacaatggc   11520
tttcagttcc tgctcactgg agcccatggc ggcagctgtt gttgatgttg cttgcttctt   11580
tatgttgtgg cgttgccggc cgagaagggc gtgcgcaggt acacggtttc gatgacgccg   11640
cggtgcggcc ggtgcacacg gaccacgtca aagacttcaa acaaaacata aagaagggtg   11700
ggctcgtcca tgggatccac ctcaaaagtc atgtctagcg cgtgggcgga gttggcgtag   11760
agaaggtttt ggcccaggtc tgtgagtgcg cccatggaca taaagttact ggagaatggg   11820
atgcgccaaa gggtgcgatc gcaaagaaac ttttctgggg taatgctgtc aactgcggtc   11880
ttgcctataa gcggataggg gaagttagca gggtaggcct gtccttcgcg catggtgggg   11940
gcaaggtagc caacaaatcc agagttgttg tgttggtgta ggatgcccac ctgttggtag   12000
tccttgtatt tagtatcatc caccacctga cggctcatgg gctggaagtt tctaaagaag   12060
gagtacatgc ggtccttgta gctctctggg atatagaagc cctggtagcc aatgttgtag   12120
ttagctagca tttgtaccag gaaccagtct ttggtcatgt tacactgggc aacgttgtaa   12180 cccctccccgt caactgagcg cttaatttca aactcgttgg gggtaagcag gcggtcattg   12240
ccaggccagc tgacagaaga gtcaaaggta atggccacct tcttaaaggt gtggttgagg   12300
taaaaggttc catctaggta gggtatagag ccagagtagg tgtaataagg gtcgtagccc   12360
gagcccagtg atgggtttc cttagtctta aggcgcgtga aggcccagcc gcggaaagcc    12420
gcccagttgc gggaggggat ggatatgggc acgttggtag cgttggcggg tatagggtag   12480
agcatgttgg cggcggagag atagtcgtta aaggactggt cgttggtgtc gtttctaagc   12540
atggcctcaa gcgtggaggc ggtgttgtgg gccatgggga agaaggtggc gtaaaggcaa   12600
atgctatcaa acttaatgct ggctccgtca acccttaggt catttcctag ggagctctgc   12660
agaaccatgt taacatcctt cctgaagttc cactcgtagg tgtatgagcc cggcaggaga   12720
aggaggtttt taatggcaaa gaacttctga ggcacctgga tgtggaaggg cacatagcga   12780
ccattgccca gcaacattga gcggtagcgc aggccagcat tgcggtggtg gttaaatggg   12840
ttgacgttgt ccatatagtc aagggaccag cgtgctccaa ggttaatgta gcagtccact   12900
aacccgggag ccaccactcg cttgttcatg tagtcgtagg tgtttgggtt atcagaaatt   12960
tttacgttgg aaggactgta ctttagcttg tcgggcaaat acagcgctat gttggagtac   13020
aggaaatttc tccacaggtt ggcatttaga ttgatttcca tggcaaaatt atttccaact   13080
cttatttcat ttttatctga aaattctgta gcatcttttt cccatccatt ttcctgacct   13140
```

```
gttttaggtt ttaccttggt aagagtctct gtattaatca cacctcccag tggaaagcag    13200
taatttggaa gttcatcttc agttccatga ttttcaataa ttctaacatc tggatcatag    13260
ctgtcaacag cctgattcca catagaaaag tacctggttc tatcaccaat ggaatcaagc    13320
aaaagctggt atgaaagctc tgtgtttctg tcttgcaaat ctacaacagc attcaactgc    13380
gatgcttggc ccgccagaac acccatatta cccgtgctgt tgtaatacat tagaccaata    13440
aaattgtccc taaaagcaat gtaattaggc ctgttgggca tagattgttg gcccattagt    13500
tctcgtgagt taccttcctt aatagtgggc atgtaagaaa tatgagtgtc tggggtttct    13560
atatctacat cttcactgta caataccact ttaggagtca agttatcacc attgcctgcg    13620
gtcgcctcag tagttgagaa aaattgcatt tccacttgac tttctagctt tccattttgt    13680
tgctttacaa gaatgccttg ccctccattt tcatttgtgg gttttgcata tgaaccgtaa    13740
catggtttca ttggggtagt cttttttaagg actctcccag ctgcatgatt aatttcagtt    13800
tcgtaccact gagattctcc tatttgaggt tcaggttgaa atgttttatc ggcatattta    13860
ggtgtttgac cttcgacacc tatttgaata ccctcctttg taatatttat accagaataa    13920
ggcgcctgcc caaatacgtg agttttttgc tgctcagctt gctcgtctac ttcgtcttcg    13980
ttgtcatcgt cctcttcttc taggtttatt tcaagagcag tagcagcttc atcccattcg    14040
caaggatttg gggcacccTT gggagccagg gcgttgtagg cagtgccaga gtagggctta    14100
aaagtagggc ccctgtccag cacgccgcgg atgtcaaagt acgtggaagc catgtccagc    14160
acacggttat cacccacagc tagggtgaac cgcgccttgt acgagtacgc agtatcctca    14220
cggtccacag ggatgaaccg cagcgtcaaa cgctgggacc ggtctgtggt cacgtcgtgc    14280
gtaggcgcca ccgtgggggtt tctaaacttg ttattcaggc tgaagtacgt ctcggtggcg    14340
cgggcaaact gcaccagccc ggggctcagg tactccgagg cgtcctggcc cgagatgtgc    14400
atgtaagacc actgcggcat catcgaaggg gtagccatct tggaaagcgg gcgcgcggcg    14460
gctcagcagc tcctctggcg gcgacatgga cgcatacatg acacacatac gacacgttag    14520
ctattcagaa gcatcgtcgg cgcttcaggg attgcacccc cagacccacg atgctgttca    14580
gtgtgctttg ccagttgcca ctggctacgg gccgcaacga tcgcggaccg ctggcggcgc    14640
ggcgcaggga cgcgcggcta ggacgggtta caacaacggc ggtcgggcct ggcagcacag    14700
gtttctgctg ggtgtcggcg gggggaggca ggtccagcgt tacgggtgtg tgctggccca    14760
gcactccggt agccatgggc gcgatgggac gggtggtggg caggccttgc tttagtgcct    14820
cctcgtacga gggaggctcg tctatttgcg tcaccagagt ttcttccctg tcggggcgcg    14880
gacgcttttc gccacgcccc tctgagacac ctgtctccac ggccggtgga ggctcctcta    14940
cgggagggcg gggatcaagc ttactgttaa tcttattttg cactgcctgg ttggccaggt    15000
ccaccacccc gctaatgcca gaggccaggc catctaccac cttttgttgg aaattttgct    15060
cttTcaactt atccctcagc atctggcctg tgctgctgtt ccaggccttg ctgccatagt    15120
tcttaacggt ggaaccgaaa ttttTaatgc cgctccacag cgagcccag ctgaaggcgc    15180 caccgctcat attgctggtg ccgatatctt gccagtttcc catgaacggg cgcgagccgt    15240
gtcgcggggc cagagacgca aagttgatgt cttccattct acaaaatagt tacaggacca    15300
agcgagcgtg agagtccaga cttttttattt tgatttttcc acatgcaact tgttttttaat    15360 cagtgtctct gcgcctgcaa ggccacggat gcaattccgg gcacggcgcc aatcgccgcg    15420
gcgatcagtg gaataaggag gggcaggata ccgccgcgca tgcgacggtg cgacgcgcgc    15480
cgccgccggt ggtgcgcacg acgcatgccg cccgtcaggc cgtggccggc catgcccctc    15540
```

```
tacggtgcat tcttcctcgg aatcccggca ccgggaaacg gaggcggcag gtgagggcca    15600
tatctgcaag aaccacaaag accggctttt aaacgatgct ggggtggtag cgcgctgttg    15660
gcagcaccag ggtcctgcct ccttcgcgag ccaccctgcg cacggaaatc ggggccagca    15720
cgggctggcg acggcgacgg cggcggcggg ttccagtggt ggttcggcgt cgggtagttg    15780
ctcgtcttct ggggcggtag gtgtagccac gatagccggg ggtaggcgca atggaaggat    15840
gtagggcata ttcgggcagt agcgcgctgg cggcgccgta cttcctcgaa ccgcgcgggc    15900
gccgggggggc tgaaacgcga aacatccacg ggtccgtttg cacctccgta gaggtcttgg    15960
acgcggccgc agcgaccgcc tgcaccgcgg catccgccac cgctgaggca accggggacg    16020
tttgtgtctc catgccctct gtggcggtgg caatactggt gctactggta gtgggtatct    16080
gaacgtccac ggtctgcacg cccagtcccg gcgccacctg cttgattggc cgcacgcgga    16140
cctcgggctc cagcccaggt tccacggtca ttttttccaa gacatcttcc agtcgctggc    16200
gcttgggtac catcagctgc acggtgggtg ccaagtcacc agactcgcgc tttaggccgc    16260
gcttttcttc ggacggtgca agcgcgggca gcacctgctg cagtgttacg ggctttaggc    16320
taggtgttgg gttgccctcg tccagcggca acgccagcat gtccttatgc cgctttccgt    16380
aggcaaactc cccgaggcgc tcgttggcct gctcaagcag gtcctcgtcg ccgtacacct    16440
catcatacac gcgcttgtag gtgcgggtgg agcgctcacc gggcgtaaag actacggtgg    16500
tgccgggtcg caaaacacgt tttacgcgtc gacctttcca ctgtaccgt cgcctgggcg    16560
cggtagcgtg cagcagttcc acctcgtcgt caagttcatc atcatcatct ttcttttct    16620
ttttgacccg cttttagcttt cggggcttgt aatcctgctc ttccttcttc gggggggccat    16680
agatctccgg cgcgatgacc tggagcatct cttctttgat tttgcgcttg gacatagctt    16740
cgttgcgcgc cgccgccgct ggatacatac aacagtacga gtctaagtag tttttcttg    16800
caatctagtt gcgcgggggg cgggtgcgca cgggcacgcg caggccgcta accgagtcgc    16860
gcacccaata cacgttgccc ctgcgaccct gagtcatagc actaatggcc gcggctgctg    16920
cggcggccgc tcgtcgcctg gacctggggg gcacagtgac aatacccgcg gccagccttc    16980
gagcggcccg catggccgcc cgtcggccgg tgcgacgtgc gcggttaagc agggccgccg    17040
ccgcgcgttg ggcggcagtg ccgggtcggc ggcggtggcg acgtgctacg cgcctccgcc    17100
gtctcttcat tttagcatag cgccgggctc cgcgcaccac ggtctgaatg gccgcgtcca    17160
ctgtggacac tggtggcggc gtgggcgtgt agttgcgcgc ctcctccacc accgcgtcga    17220
tggcgtcatc gacggtggtg cgcccagtgc ggccgcgttt gtgcgcgccc cagggcgcgc    17280
ggtagtgccc gcgcacgcgc actggtgtt ggtcggagcg cttcttggcc ccgccaaaca    17340
tcttgcttgg gaagcgcagg ccccagcctg tgttattgct gggcgatata aggatggaca    17400
tgcttgctca aaaagtgcgg ctcgatagga cgcgcggcga gactatgccc agggcctttgt    17460
aaacgtaggg gcaggtgcgg cgtctggcgt cagtaatggt cactcgctgg actcctccga    17520
tgctgttgcg cagcggtagc gtcccgtgat ctgtgagagc aggaacgttt tcactgacgg    17580
tggtgatggt gggggctggc gggcgcgcca aaatctggtt ctcgggaaag cgattgaaca    17640
cgtgggtcag agaggtaaac tggcggatga gttgggagta gacggcctgg tcgttgtaga    17700
agctcttgga gtgcacgggc aacagctcgg cgcccaccac cggaaagttg ctgatctggc    17760
gcgtggagcg gaaggtcacg gggtcttgca tcatgtctgg caacgaccag tagacctgct    17820
ccgagccgca ggttacgtca ggagtgcaaa gcagggtcca tgagcggatt ccggtctgag    17880
```

```
ggtcgccgta gttgtatgca aggtaccagc tgcggtactg ggtgaaggtg ctgtcattgc    17940
ttattaggtt gtaactgcgt ttcttgctgt cctctgtcag gggtttgatc accggtttct    18000
tctgaggctt ctcgacctcg ggttgcgcag cgggggcggc agcttcggcc gctgcttcgg    18060
cctcagcgcg cttctcctca gcccgtgtgg caaaggtgtc ccgcgaatg gcatgatcgt     18120
tcatgtcctc caccggctgc attgccgcgc ctgccgcgtt ggagttctct tccgcgccgc    18180
tgccactgct gttgctgccg cctgcgccac ccccgccctg ttcggtgtca tctttcaagc    18240
tcgcctggta ggcgtccaca tccaacagtg cgggaatgtt accaccctcc agatcatcgt    18300
aggtgatcct aaagccctcc tggaagggtt gccgcttgcg gatgcccaac aagttgctca    18360
ggcggctgtg ggtgaagtcc accccgcatc ctggcagcaa aatgatgtct ggatggaagg    18420
cttcgtttgt atatacccca ggcatgacaa gaccagtgac ggggtcaaac cccagtctga    18480
agttgcgggt gtcaaacttt accccgatgt cgctttccag aaccccgttc tgtctgccca    18540
cttttcaagta gtgctccacg atcgcgttgt tcataaggtc tatggtcatg gtctcggagt    18600
agttgccctc gggcagcgtg aactccaccc actcgtattt cagctccacc tgattgtcct    18660
tagtaggcaa gcgcgacacc atcacccgcg ccttaaactt attggtaaac atgaactcgt    18720
tcacatttgg catgttggta tgcaggatgg ttttcaggtc gccgcccag tgcgaccggt     18780
cgtcaagatt gatggtctgt gtgcttgcct ccccgggct gtagtcattg ttttgaatga     18840
ccgtggtcag aaagttgctg tggtcgttct ggtagttcag ggatgccaca tccgttgact    18900
tgttgtccac caggtacaca cgggtggtgt cgaataggg tgccaactca gagtaacgga    18960
tgctgtttct cccccggta ggccgcaggt accgcggagg cacaaacggc gggtccaggg     19020
gagcatcgaa gggagaaccc agcgccgccg ccactggcgc cgcgctcacc acactctcgt    19080
aggagggagg aggaccttcc tcatacatcg ccgcgcgccg catactaagg ggaatacaag    19140
aaaaccaacg ctcggtgcca tggccttggt gagttttta ttttgcatca tgcttttttt    19200
ttttttaaaac attctcccca gcctggggcg aaggtgcgca acggggttgc cactccctcc    19260
caaatccagg acgctgctgt cgtctgccga gtcatcgtcc tcccacacca gaccccgctg    19320
acggtcgtgc ctttgacgac gggtgggcgg gcgcgggcct ggcacgtccc tgtgctcctg    19380
cgcgtacgtc ttccatctac tcatcttgtc cactaggctc tctatcccgt tgttgggaaa    19440
tgccggaggc aggttttttt cgcgctgcgg ctgcagcagc gagttgttta ggtactcctc    19500
ctcgcccagc aggcgcgggc gggtggtgcg agtgctggta agagaccccta tcaagcttgg    19560
aaatgggcta ctagcatctg accgcgggc cgcagcgcct agatcggaca agctgcttgg    19620
cctgcggaag cttttccttc gcagcgccgc ctctgcctgc tcgcgctgtt gcaactctag    19680
cagggtctgc ggttgcgggg aaaacacgct gtcgtctatg tcgtcccaga ggaatccatc    19740
gttaccctcg ggcacctcga atccccggt gtagaaacca gggggcggta gccagtgcgg     19800
gttcaagatg gcattggtga aatactcggg gttcacggcg gccgcgcgat gcaagtagtc    19860
cattaggcgg ttgataaacg gccggtttga ggcatacatg cccggttcca tgttgcgcgc    19920
ggtcatgtcc agcgccacgc tgggcgttac cccgtcgcgc atcaggttaa ggctcacgct    19980
ctgctgcacg tagcgcaaaa tgcgctcctc ctcgctgttt aaactgtgca acgaggggat    20040
cttctgccgc cggttggtca gcaggtagtt tagggttgcc tccaggctgc ccgtgtcctc    20100
ctgccccagc gcgcggctga cacttgtaat ctcctggaaa gtatgctcgt ccacatgcgc    20160
ctgacctatg gcctcgcggt acagtgtcag caagtgacct aggtatgtgt cccgggacac    20220
gctgccactg tccgtgaagg gcgctattag cagcagcaac aggcgcgagt tgggcgtcag    20280
```

```
caagctagac acggtcgcgc ggtcgcctgt gggagcccgc accccccaca gcccctgcaa   20340
gtttttgaaa gcctggctca ggtttacggt ctgcaggcct tgtctactgg tctggaaaaa   20400
atagtctggc ccagactggt cacctcact ttgcggtgtc tcagtcacca ttagccgcag    20460
tgcgctcaca aagttggtgt agtcctcctg tccccgcggc acgttggcgg gctgtgtact   20520
caggaaggcg tttagtgcaa ccatggagcc caggttgccc tgctgctgcg cgcgctcacg   20580
ctgcgccacg gcctcgcgca catcccccac cagccggtcc aggttggtct gcacgttgcc   20640
gctgttgtaa cgagccacgc gctgaagcag cgcgtcgtag accaggccgg cctcgtcggg   20700
ccggatggcc ctgttttcgg ccagcgcgtt tacgatcgcc agcaccttct cgtgcgtggg   20760
gtttgcgcgc gccgggacca ccgcttccag aattgcggag agccggttgg cctgcggctg   20820
ctgccggaac gcgtcaggat tgcgcgcagt cagcgacatg atgcggtcca tgacctggcg   20880
ccagtcgtcc gtggagttaa ggccggacgg ctggctctgc agcgccgccc gcaccgccgg   20940
gtccgttgcg tcttgcatca tctgatcaga acatcaccg cttagtactc gccgtcctct    21000
ggctcgtact catcgtcctc gtcatattcc tccacgccgc cgacgttgcc agcgcgcgcg   21060
ggtgccaccg ccagcccagg tccggcccca gctgcctcca gggcgcgtcg gcttggggcc   21120
cagcgcaggt cagcgcccgc gtcaaagtag gactcggcct ctctatcgcc gctgcccgtg   21180
ccagccaggg ccctttgcag gctgtgcatc agctcgcggt cgctgagctc gcgccgccgg   21240
ctcacgctca cggccttgtg gatgcgctcg ttgcgataaa cgcccaggtc gtcgctcaag   21300
gtaagcacct tcagcgccat cgcatgtag aacccctcga tctttacctc cttgtctatg    21360
ggaacgtaag gggtatggta tatcttgcgg gcgtaaaact tgcccaggct aagcatggaa   21420
tagttgatgg cggccacctt gtcagccagg ctcaagctgc gctcctgcac cactatgctc   21480
tgcaggatgt ttatcaaatc gagcagccag cggccctcgg gctctactat gtttagcagc   21540
gcatccctga atgcctcgtt gtccctgctg tgctgcacta taggaacag ctgcgccatg    21600
agcggcttgc tatttgggtt ttgctccagc gcgcttacaa agtcccacag atgcatcagt   21660
cctatagcca cctcctcgcg cgccacaagc gtacgcacgt ggttgttaaa gctttttga    21720
aagttaatct cctggttcac cgtctgctcg tatgcggtta ccaggtcggc ggccgccacg   21780
tgtgcgcgcg cgggactaat cccggttcgc gcgtcgggct caaagtcctc ctcgcgcagc   21840
aaccgctcgc gattcaggcc atgccgcagc tcgcgccctg cgtggaactt tcgatcccgc   21900
atctcctcgg gctcctctcc ctcgcggtcg cgaaacaggt tctgccgcgg cacgtacgcc   21960
tcacgcgtat cacgcttcag ctgcacccctt gggtaccgct caggagaggg cgctcctagc   22020
cgcgccaggc cctcgcccctc ctccaagtcc aggtagtgcc gggcccggcg ccgcgggggt   22080
tcgtaatcac catctgctgc cgcgtcaacc gcggatgtcg cccctcctga cgcggtagga   22140
ggaggggagg gtgccctgca tgtctgccgc tgctcttgct cttgccgctg ctgaggaggg   22200
gggcgcatct gccgcagcac cggatgcatc tgggaaaagc aaaaaggggg ctcgtccctg   22260
tttccggagt aatttgcaag cggggtcttg catgacgggg aggcaaaccc ccgttcgccg   22320
cagtccggcc ggtccgagac tcgaaccggg ggtcccgcga ctcaacccctt ggaaaataac   22380
cctccggcta cagggagcga gccacttaat gctttcgctt tccagcctaa ccgcttacgc    22440
tgcgcgcggc cagtggccaa aaaagctagc gcagcagccg ccgcgcctgg aaggaagcca   22500
aaaggagcac tccccgttg tctgacgtcg cacacctggg ttcgacacgc gggcggtaac     22560
cgcatggatc acggcggacg gccggatacg gggctcgaac cccggtcgtc cgccatgata   22620
```

-continued

| | |
|---|---|
| cccttgcgaa tttatccacc agaccacgga agagtgcccg cttacaggct ctccttttgc | 22680 |
| acggtagagc gtcaacgatt gcgcgcgcct gaccggccaa agcgtcccga ccatggagca | 22740 |
| cttttttgccg ctgcgcaaca tctggaaccg cgtccgcgac tttccgcgcg cctccaccac | 22800 |
| cgccgccggc atcacctgga tgtccaggta catctacgga tatcatcgcc ttatgttgga | 22860 |
| agatctcgcc cccggagccc cggccaccct acgctggccc ctctaccgcc agccgccgcc | 22920 |
| gcactttttg gtgggatacc agtacctggt gcggacttgc aacgactacg tatttgactc | 22980 |
| gagggcttac tcgcgtctca ggtacaccga gctctcgcag ccgggtcacc agaccgttaa | 23040 |
| ctggtccgtt atggccaact gcacttacac catcaacacg ggcgcatacc accgctttgt | 23100 |
| ggacatggat gacttccagt ctaccctcac gcaggtgcag caggccatat agccgagcg | 23160 |
| cgttgtcgcc gacctagccc tgcttcagcc gatgaggggc ttcggggtca cacgcatggg | 23220 |
| aggaagaggg cgccacctac ggccaaactc cgccgccgcc gcagcgatag atgcaagaga | 23280 |
| tgcaggacaa gaggaaggag aagaagaagt gccggtagaa aggctcatgc aagactacta | 23340 |
| caaagacctg cgccgatgtc aaaacgaagc ctggggcatg gccgaccgcc tgcgcattca | 23400 |
| gcaggccgga cccaaggaca tggtgcttct gtcgaccatc cgccgtctca agaccgccta | 23460 |
| ctttaattac atcatcagca gcacctccgc cagaaacaac cccgaccgcc gcccgctgcc | 23520 |
| gcccgccacg tgctcagcc taccttgcga ctgtgactgg ttagacgcct ttctcgagag | 23580 |
| gttttccgat ccggtcgatg cggactcgct caggtccctc ggcggcggag tacctacaca | 23640 |
| acaattgttg agatgcatcg ttagcgccgt atccctgccg catggcagcc ccccgccaac | 23700 |
| ccataaccgg gacatgacgg gcggcgtctt ccaactgcgc ccccgcgaga acggccgcgc | 23760 |
| cgtcaccgag accatgcgcc gtcgccgcgg ggagatgatc gagcgctttg tcgaccgcct | 23820 |
| cccggtgcgc cgtcgtcgcc gccgtgtccc ccctccccca ccgccgccag aagaagaaga | 23880 |
| aggggaggcc cttatggaag aggagattga agaagaagaa gaggcccctg tagcctttga | 23940 |
| gcgcgaggtg cgcgacactg tcgccgagct catccgtctt ctggaggagg agttaaccgt | 24000 |
| gtcggcgcgc aactcccagt ttttcaactt cgccgtggac ttctacgagg ccatggagcg | 24060 |
| ccttgaggcc ttgggggata tcaacgaatc cacgttgcga cgctgggtta tgtacttctt | 24120 |
| cgtggcagaa cacaccgcca ccaccctcaa ctacctcttt cagcgcctgc gaaactacgc | 24180 |
| cgtcttcgcc cggcacgtgg agctcaatct cgcgcaggtg gtcatgcgcg cccgcgatgc | 24240 |
| cgaaggggc gtggtctaca gccgcgtctg gaacgaggga ggcctcaacg ccttctcgca | 24300 |
| gctcatggcc cgcatttcca acgacctcgc cgccaccgtg gagcgagccg gacgcggaga | 24360 |
| tctccaggag gaagagatcg agcagttcat ggccgagatc gcctatcaag acaactcagg | 24420 |
| agacgtgcag gagattttgc gccaggccgc cgtcaacgac accgaaattg attctgtcga | 24480 |
| actctctttc aggctcaagc tcaccgggcc cgtcgtcttc acgcagaggc gccagattca | 24540 |
| ggagatcaac cgccgcgtcg tcgcgttcgc cagcaaccta cgcgcgcagc accagctcct | 24600 |
| gcccgcgcgc ggcgccgacg tgcccctgcc ccctctcccg gcgggtccgg agccccccct | 24660 |
| acctccgggg gctcgcccgc gtcaccgctt ttagatgcat catccaagga cacccccgcg | 24720 |
| gcccaccgcc cgccgcgcgg taccgtagtc gcgccgcggg gatgcggcct cttgcaagcc | 24780 |
| atcgacgccc ccaccaacca gccccctggaa attaggtatc acctggatct agcccgcgcc | 24840 |
| ctgacccgtc tatgcgaggt aaacctgcag gagctcccgc ctgacctgac gccgcgggag | 24900 |
| ctccagacca tggacagctc ccatctgcgc gatgttgtca tcaagctccg accgccgcgc | 24960 |
| gcggacatct ggactttggg ctcgcgcggc gtggtggtcc gatccaccgt aactcccctc | 25020 |

```
gagcagccag acggtcaagg acaagcagcc gaagtagaag accaccagcc aaacccgcca   25080 ggcgagggc tcaaattccc actctgcttc cttgtgcgcg gtcgtcaggt caacctcgtg    25140
caggatgtac agcccgtgca ccgctgccag tactgcgcac gttttttacaa agccagcac   25200 gagtgttcgg cccgtcgcag ggacttctac tttcaccaca tcaatagcca ctcctccaat   25260
tggtggcgga gatccagtt cttcccgatc ggctcgcatc ctcgcaccga gcgtctcttt    25320
gtcacctacg atgtagagac ctatacttgg atgggggcct ttgggaagca gctcgtgccc   25380
ttcatgctgg tcatgaagtt cggcggagat gagcctctag tgactgccgc gcgagaccta   25440
gccgcgaacc ttggatggga ccgctgggaa caagacccgc ttaccttcta ctgcatcacc   25500
ccagaaaaaa tggccatagg tcgccagttt aggacctttc gcgaccacct gcaaatgcta   25560
atggcccgtg acctgtggag ctcattcgtc gcttccaacc ctcatcttgc agactgggcc   25620
ctttcagagc acgggctcag ctcccctgaa gagctcacct acgaggaact taaaaaattg   25680
ccttccatca agggcatccc gcgcttcttg aactttaca ttgtgggcca caacatcaac    25740
ggctttgacg agatcgtgct cgccgcccag gtaattaaca accgttccga ggtgccggga   25800 ccccttccgca tcacacgcaa ctttatgcct cgcgcgggaa agatactctt caacgatgtc   25860
accttcgccc tgccaaatcc gcgttccaaa agcgcacgg acttttttgct ctgggagcag   25920 ggcggatgcg acgacactga cttcaaatac cagtacctca agtcatggt cagggacacc    25980 tttgcgctca cccacacctc gctccggaag gccgcgcagg catacgcgct acccgtagaa   26040
aagggatgct gcgcctacca ggccgtcaac cagttctaca tgctaggctc ttaccgttcg   26100
gaggccgacg ggtttccgat ccaagagtac tggaaagacc gcgaagagtt tgtcctcaac   26160
cgcgagctgt ggaaaaaaaa gggacaggat aagtatgaca tcatcaagga aaccctggac   26220
tactgcgccc tagacgtgca ggtcaccgcc gagctggtca acaagctgcg cgactcctac   26280
gcctccttcg tgcgtgacgc ggtaggtctc acagacgcca gcttcaacgt cttccagcgt   26340
ccaaccatat catccaactc acatgccatc ttcaggcaga tagtcttccg agcagagcag   26400
cccgcccgta gcaacctcgg tcccgacctc ctcgctccct cgcacgaact atacgattac   26460
gtgcgcgcca gcatccgcgg tggaagatgc taccctacat atcttggaat actcagagag   26520
cccctctacg tttacgacat ttgcggcatg tacgcctccg cgctcaccca ccccatgcca   26580
tggggtcccc cactcaaccc atacgagcgc gcgcttgccg cccgcgcatg gcagcaggcg   26640
ctagacttgc aaggatgcaa gatagactac ttcgacgcgc gcctgctgcc cggggtctt    26700 accgtggacg cagacccccc ggacgagacg cagctagacc ccctaccgcc attctgctcg   26760
cgcaagggcg gccgctctg ctggaccaac gagcgcctac gcggagaggt agccaccagc    26820
gttgaccttg tcaccctgca caaccgcggt tggcgcgtgc acctggtgcc cgacgagcgc   26880
accaccgtct ttcccgaatg gcggtgcgtt gcgcgcgaat acgtgcagct aaacatcgcg   26940
gccaaggagc gcgccgatcg cgacaaaaac caaacccctgc gctccatcgc caagttgctg   27000
tccaacgccc tctacgggtc gtttgccacc aagcttgaca caaaaagat tgtctttttct   27060 gaccagatgg atgcggccac cctcaaaggc atcaccgcgg gccaggtgaa tatcaaatcc   27120
tcctcgtttt tggaaactga caatcttagc gcagaagtca tgcccgcttt tcagagggag   27180
tactcacccc aacagctggc cctcgcagac agcgatgcg aagagagtga ggacgaaacgc    27240 gccccccacccc ccttttatag cccccctca ggaacacccg gtcacgtggc ctacacctac    27300
aaaccaatca ccttccttga tgccgaagag ggcgacatgt gtcttcacac cctggagcga   27360
```

```
gtggaccccc tagtggacaa cgaccgctac ccctcccact tagcctcctt cgtgctggcc    27420
tggacgcgag cctttgtctc agagtggtcc gagtttctat acgaggagga ccgcggaaca    27480
ccgctcgagg acaggcctct caagtctgta tacggggaca cggacagcct tttcgtcacc    27540
gagcgtggac accggctcat ggaaaccaga ggtaagaaac gcatcaaaaa gcatggggga    27600
aacctggttt tgaccccga acggccagag ctcacctggc tcgtggaatg cgagaccgtc    27660
tgcggggcct gcggcgcgga tgcctactcc ccggaatcgg tatttctcgc gcccaagctc    27720
tacgccctca aaagtctgca ctgcccctcg tgcggcgcct cctccaaggg caagctgcgc    27780
gccaagggcc acgccgcgga ggggctggac tatgacacca tggtcaaatg ctacctggcc    27840
gacgcgcagg gcgaagaccg gcagcgcttc agcaccagca ggaccagcct caagcgcacc    27900
ctggccagcg cgcagcccgg agcgcacccc ttcaccgtga cccagactac gctgacgagg    27960
accctgcgcc cgtggaaaga catgaccctg gcccgtctgg acgagcaccg actactgccg    28020
tacagcgaaa gccgccccaa cccgcgaaac gaggagatat gctggatcga gatgccgtag    28080
agcaggtgac cgagctgtgg gaccgcctgg aactgcttgg tcaaacgctc aaaagcatgc    28140
ctacggcgga cggtctcaaa ccgttgaaaa actttgcttc cttgcaagaa ctgctatcgc    28200
tgggcggcga gcgccttctg gcggatttgg tcagggaaaa catgcgagtc agggacatgc    28260
ttaacgaagt ggccccctg ctcagggatg acggcagctg cagctctctt aactaccagt    28320
tgcacccggt aataggtgtg atttacgggc ccaccggctg cggtaagtcg cagctgctca    28380
ggaacctgct tcttcccag ctgatctccc ctaccccgga aaccgttttc ttcatcgccc    28440
cgcaggtaga catgatcccc ccatctgaac tcaaagcgtg ggaaatgcaa atctgtgagg    28500
gtaactacgc ccctgggccg gatggaacca ttataccgca gtctggcacc ctccgcccgc    28560
gctttgtaaa aatggcctat gacgatctca tcctggaaca caactatgac gttagtgatc    28620
ccagaaatat cttcgcccag gccgccgccc gtgggcccat tgccatcatt atggacgaat    28680
gcatggaaaa tcttggaggt cacaagggcg tctccaagtt cttccacgca tttccttcta    28740
agctacatga caaatttccc aagtgcaccg gatacactgt gctggtggtt ctgcacaaca    28800
tgaatccccg gagggatatg gctgggaaca tagccaacct aaaaatacag tccaagatgc    28860
atctcatatc cccacgtatg cacccatccc agcttaaccg ctttgtaaac acttacacca    28920
agggcctgcc cctggcaatc agcttgctac tgaaagacat ttttaggcac cacgcccagc    28980
gctcctgcta cgactggatc atctacaaca ccaccccgca gcatgaagct ctgcagtggt    29040
gctacctcca ccccagagac gggcttatgc ccatgtatct gaacatccag agtcaccttt    29100
accacgtcct ggaaaaaata cacaggaccc tcaacgaccg agaccgctgg tcccgggcct    29160
accgcgcgcg caaaaccct aaataaagac agcaagacac ttgcttgatc caaatccaaa    29220
cagagtctgg tttttattt atgttttaaa ccgcattggg aggggaggaa gccttcaggg    29280
cagaaacctg ctggcgcaga tccaacagct gctgagaaac gacattaagt tcccgggtca    29340
aagaatccaa ttgtgccaaa agagccgtca acttgtcatc gcgggcggat gaacgggaag    29400
ctgcactgct tgcaagcggg ctcaggaaag caaagtcagt cacaatcccg cgggcggtgg    29460
ctgcagcggc tgaagcggcg gcggaggctg cagtctccaa cggcgttcca gacacggtct    29520
cgtaggtcaa ggtagtagag tttgcgggca ggacggggcg accatcaatg ctggagccca    29580
tcacattctg acgcaccccg gcccatgggg gcatgcgcgt tgtcaaatat gagctcacaa    29640
tgcttccatc aaacgagttg gtgctcatgg cggcggcggc tgctgcaaaa cagatacaaa    29700
actacataag accccacct tatatattct ttcccaccct tannntaata gtaatcaatt    29760
```

```
acggggtcat tagttcatag cccatatatg gagttccgcg ttggtaaatg gcccgcctgg    29820
ctgaccgccc aacgaccccc gcccattgac gtcaataatg acgtatgttc ccatagtaac    29880
gccaataggg actttccatt gacgtcaatg ggtggagtat ttacggtaaa ctgcccactt    29940
ggcagtacat caagtgtatc atatgccaag tacgccccct attgacgtca atgacggtaa    30000
atggcccgcc tggcattatg cccagtacat gaccttatgg gactttccta cttggcagta    30060
catctacgta ttagtcatcg ctattaccat ggtgatgcgg ttttggcagt acatcaatgg    30120
gcgtggatag cggtttgact cacggggatt tccaagtctc cacccccattg acgtcaatgg    30180
```
(corrected) 
```
acggggtcat tagttcatag cccatatatg gagttccgcg ttggtaaatg gcccgcctgg    29820
ctgaccgccc aacgaccccc gcccattgac gtcaataatg acgtatgttc ccatagtaac    29880
gccaataggg actttccatt gacgtcaatg ggtggagtat ttacggtaaa ctgcccactt    29940
ggcagtacat caagtgtatc atatgccaag tacgccccct attgacgtca atgacggtaa    30000
atggcccgcc tggcattatg cccagtacat gaccttatgg gactttccta cttggcagta    30060
catctacgta ttagtcatcg ctattaccat ggtgatgcgg ttttggcagt acatcaatgg    30120
gcgtggatag cggtttgact cacggggatt tccaagtctc cacccccattg acgtcaatgg    30180
gagtttgttt tggcaccaaa atcaacggga ctttccaaaa tgtcgtaaca actccgcccc    30240
attgacgcaa atgggcggta ggcgtgtacg gtgggaggtc tatataagca gagctggttt    30300
agtgaaccgt cagatccgct agagatctgg taccaccatg gctgccatct ctacttccat    30360
ccctgtaatt tcacagcccc agttcacagc catgaatgaa ccacagtgct ctacaacga    30420
gtccattgcc ttctttttata accgaagtgg aaagcatctt gccacagaat ggaacacagt    30480
cagcaagctg gtgatgggac ttggaatcac tgtttgtatc ttcatcatgt tggccaacct    30540
attggtcatg gtggcaatct atgtcaaccg ccgcttccat tttcctatt attacctaat    30600
ggctaatctg gctgctgcag acttctttgc tgggttggcc tacttctatc tcatgttcaa    30660
cacaggaccc aatactcgga gactgactgt tagcacatgg ctccttcgtc agggcctcat    30720
tgacaccagc ctgacggcat ctgtggccaa cttactggct attgcaatcg agaggcacat    30780
tacggttttc cgcatgcagc tccacacacg gatgagcaac cggcgggtag tggtggtcat    30840
tgtggtcatc tggactatgg ccatcgttat gggtgctata cccagtgtgg gctgaactg    30900
tatctgtgat attgaaaatt gttccaacat ggcacccctc tacagtgact cttacttagt    30960
cttctgggcc attttcaact tggtgacctt tgtggtaatg gtggttctct atgctcacat    31020
cttttggctat gttcgccaga ggactatgag aatgtctcgg catagttctg acccccggcg    31080
gaatcgggat accatgatga gtcttctgaa gactgtggtc attgtgcttg ggcctttat    31140
catctgctgg actcctggat tggtttttgtt acttctagac gtgtgctgtc cacagtgcga    31200
cgtgctggcc tatgagaaat tcttccttct ccttgctgaa ttcaactctg ccatgaaccc    31260
catcatttac tcctaccgcg acaaagaaat gagcgccacc tttaggcaga tcctctgctg    31320
ccagcgcagt gagaaccccca ccggccccac agaaggctca gaccgctcgg cttcctccct    31380
caaccacacc atcttggctg gagttcacag caatgatcac tctgtggttt atccctatga    31440
cgtccccgac tatgcctgac tcgagcctaa gcttctagat aagatatccg atcnntggag    31500
ttcgtgaccg ccgccgggat cactctcggc atggacgagc tgtacaagtc cggactcaga    31560
tccaccggat ctagataact gatcataatc agccatacca catttgtaga ggttttactt    31620
gctttaaaaa acctcccaca cctcccctg aacctgaaac ataaaatgaa tgcaattgtt    31680
gttgttaact tgtttattgc agcttataat ggttacaaat aaagcaatag catcacaaat    31740
ttcacaaata aagcattttt ttcactgcat tctagttgtg gtttgtccaa actcatcaat    31800
gtatcttaac gcgnnntaat agtaatcaat tacgggtca ttagttcata gcccatatat    31860
ggagttccgc gttacataac ttacggtaaa tggcccgcct ggctgaccgc caacgaccc    31920
ccgcccattg acgtcaataa tgacgtatgt tcccatagta acgccaatag ggactttcca    31980
ttgacgtcaa tgggtggagt atttacggta aactgcccac ttggcagtac atcaagtgta    32040
tcatatgcca agtacgcccc ctattgacgt caatgacggt aaatggcccg cctggcatta    32100
```

```
tgcccagtac atgaccttat gggactttcc tacttggcag tacatctacg tattagtcat    32160
cgctattacc atggtgatgc ggttttggca gtacatcaat gggcgtggat agcggtttga    32220
ctcacgggga tttccaagtc tccaccccat tgacgtcaat gggagtttgt tttggcacca    32280
aaatcaacgg gactttccaa aatgtcgtaa caactccgcc ccattgacgc aaatgggcgg    32340
taggcgtgta cggtgggagg tctatataag cagagctggt ttagtgaacc gtcagatccg    32400
ctagcgctac cggtcgccac catggtgagc aagggcgagg agctgttcac cggggtggtg    32460
cccatcctgg tcgagctgga cggcgacgta acggccaca agttcagcgt gtccggcgag    32520
ggcgagggcg atgccaccta cggcaagctg accctgaagt tcatctgcac caccggcaag    32580
ctgcccgtgc cctggcccac cctcgtgacc accctgacct acggcgtgca gtgcttcagc    32640
cgctaccccg accacatgaa gcagcacgac ttcttcaagt ccgccatgcc cgaaggctac    32700
gtccaggagc gcaccatctt cttcaaggac gacggcaact acaagacccg cgccgaggtg    32760
aagttcgagg gcgacaccct ggtgaaccgc atcgagctga agggcatcga cttcaaggag    32820
gacggcaaca tcctggggca caagctggag tacaactaca acagccacaa cgtctatatc    32880
atggccgaca agcagaagaa cggcatcaag gtgaacttca agatccgcca caacatcgag    32940
gacggcagcg tgcagctcgc cgaccactac cagcagaaca cccccatcgg cgacggcccc    33000
gtgctgctgc ccgacaacca ctacctgagc acccagtccg ccctgagcaa agaccccaac    33060
gagaagcgcg atcacatggt cctgctggag ttcgtgaccg ccgccgggat cactctcggc    33120
atggacgagc tgtacaagtc cggactcaga tccaccggat ctagataact gatcataatc    33180
agccatacca catttgtaga ggttttactt gctttaaaaa acctcccaca cctcccctg    33240 aacctgaaac ataaaatgaa tgcaattgtt gttgttaact tgtttattgc agcttataat    33300
ggttacaaat aaagcaatag catcacaaat ttcacaaata agcattttt ttcactgcat    33360 tctagttgtg gtttgtccaa actcatcaat gtatcttaac gcgnnnttac gcgctatgag    33420
taacacaaaa ttattcagat ttcacttcct cttattcagt tttcccgcga aaatggccaa    33480
atcttactcg gttacgccca aatttactac aacatccgcc taaaaccgcg cgaaaattgt    33540
cacttcctgt gtacaccggc gcacaccaaa acgtcactt ttgccacatc cgtcgcttac    33600
atgtgttccg ccacacttgc aacatcacac ttccgccaca ctactacgtc acccgccccg    33660
ttcccacgcc cgcgccacgt cacaaactcc accccctcat tatcatattg gcttcaatcc    33720
aaaaggggca gagagctgga agggannntt aattaannnn nnnnnnnnn nnnnnnnnn    33780 nnnnnnnnn nnncggcgca ttaagcgcgc gggtgtggtg gttacgcgca gcgtgaccgc    33840
tacacttgcc agcgccctag cgcccgctcc tttcgctttc ttcccttcct ttctcgccac    33900
gttcgccggc tttccccgtc aagctctaaa tcggggggctc cctttagggt tccgatttag    33960
agctttacgg cacctcgacc gcaaaaaact tgatttgggt gatggttcac gtagtgggcc    34020
atcgccctga tagacggttt ttcgcccttt gacgttggag tccacgttct ttaatagtgg    34080
actcttgttc caaactggaa caacactcaa ccctatcgcg gtctattctt ttgatttata    34140
agggatgttg ccgatttcgg cctattggtt aaaaaatgag ctgatttaac aaaaattta    34200 acaaaattca gaagaactcg tcaagaaggc gatagaaggc gatgcgctgc gaatcgggag    34260
cggcgatacc gtaaagcacg aggaagcggt cagcccattc gccgccaagc tcttcagcaa    34320
tatcacgggt agccaacgct atgtcctgat agcggtccgc cacacccagc cggccacagt    34380
cgatgaatcc agaaaagcgg ccattttcca ccatgatatt cggcaagcag gcatcgccat    34440
gggtcacgac gagatcctcg ccgtcgggca tgctcgcctt gagcctggcg aacagttcgg    34500
```

```
ctggcgcgag cccctgatgc tcttcgtcca gatcatcctg atcgacaaga ccggcttcca    34560
tccgagtacg tgctcgctcg atgcgatgtt tcgcttggtg gtcgaatggg caggtagccg    34620
gatcaagcgt atgcagccgc cgcattgcat cagccatgat ggatactttc tcggcaggag    34680
caaggtgaga tgacaggaga tcctgccccg gcacttcgcc caatagcagc cagtcccttc    34740
ccgcttcagt gacaacgtcg agcacagctg cgcaaggaac gcccgtcgtg gccagccacg    34800
atagccgcgc tgcctcgtct tgcagttcat tcagggcacc ggacaggtcg gtcttgacaa    34860
aaagaaccgg gcgcccctgc gctgacagcc ggaacacggc ggcatcagag cagccgattg    34920
tctgttgtgc ccagtcatag ccgaatagcc tctccaccca gcggccgga gaacctgcgt     34980 gcaatccatc ttgttcaatc atgcgaaacg atcctcatcc tgtctcttga tcagagcttg    35040
atcccctgcg ccatcagatc cttggcggcg agaaagccat ccagtttact ttgcagggct    35100
tcccaacctt accagagggc gccccagctg gcaattccgg ttcgcttgct gtccataaaa    35160
ccgcccagtc tagctatcgc catgtaagcc cactgcaagc tacctgcttt ctctttgcgc    35220
ttgcgttttc ccttgtccag atagcccagt agctgacatt catccggggt cagcaccgtt    35280
tctgcggact ggctttctac gtgaaaagga tctaggtgaa gatcctttt nnnnnncaac     35340 aacgttgcgc aaactattaa ctggcgaact acttactcta gcttcccggc aacaattaat    35400
agactggatg gaggcggata agttgcagg accacttctg cgctcggccc ttccggctgg     35460
ctggtttatt gctgataaat ctggagccgg tgagcgtggg tctcgcggta tcattgcagc    35520
actgggccca gatggtaagc cctcccgtat cgtagttatc tacacgacgg ggagtcaggc    35580
aactatggat gaacgaaata gacagatcgc tgagataggt gcctcactga ttaagcattg    35640
gtaactgtca gaccaagttt actcatatat actttagatt gatttaaaac ttcattttta    35700
atttaaaagg atctaggtga agatcctttt tgataatctc atgaccaaaa tcccttaacg    35760
tgagttttcg ttccactgag cgtcagaccc cgtagaaaag atcaaaggat cttcttgaga    35820
tccttttttt ctgcgcgtaa tctgctgctt gcaaacaaaa aaaccaccgc taccagcggt    35880
ggtttgtttg ccggatcaag agctaccaac tcttttccg aaggtaactg gcttcagcag     35940
agcgcagata ccaaatactg tccttctagt gtagccgtag ttaggccacc acttcaagaa    36000
ctctgtagca ccgcctacat acctcgctct gctaatcctg ttaccagtgg ctgctgccag    36060
tggcgataag tcgtgtctta ccgggttgga ctcaagacga tagttaccgg ataaggcgca    36120
gcggtcgggc tgaacggggg gttcgtgcac acagcccagc ttggagcgaa cgacctacac    36180
cgaactgaga tacctacagc gtgagcattg agaaagcgcc acgcttcccg aagggagaaa    36240
ggcggacagg tatccggtaa gcggcaggGt cggaacagga gagcgcacga gggagcttcc    36300
agggggaaac gcctggtatc tttatagtcc tgtcgggttt cgccacctct gacttgagcg    36360
tcgatttttg tgatgctcgt caggggggcg gagcctatgg aaaaacgcca gcaacgcggc    36420
ctttttacgg ttcctggcct tttgctggcc ttttgctcac atgttctttc ctgcgttatc    36480
ccctgattct gtggataacc gtattaccgc ctttgagtga gctgataccg ctcgccgcag    36540
ccgaacgacc gagcgcagcg agtcagtgag cgaggaagcg gaagagcgcc tgatgcggta    36600
ttttctcctt acgcatctgt gcggtatttc acaccgcata tggtgcactc tcagtacaat    36660
ctgctctgat gccgcatagt taagccagta tacactccgc tatcgctacg tgactgggtc    36720
atggctgcgc cccgacaccc gccaacaccc gctgacgcgc cctgacgggc ttgtctgctc    36780
ccggcatccg cttacagaca agctgtgacc gtctccggga gctgcatgtg tcagaggttt    36840
```

```
tcaccgtcat caccgaaacg cgcgaggcag ctgcggtaaa gctcatcagc gtggtcgtga    36900
agcgattcac agatgtctgc ctgttcatcc gcgtccagct cgttgagttt ctccagaagc    36960
gttaatgtct ggcttctgat aaagcgggcc atgttaaggg cggtttttc ctgtttggtc     37020 acttgatgcc tccgtgtaag ggggaatttc tgttcatggg ggtaatgata ccgatgaaac    37080
gagagaggat gctcacgata cgggttactg atgatgaaca tgcccggtta ctggaacgtt    37140
gtgagggtaa acaactggcg gtatggatgc ggcgggacca gagaaaaatc actcagggtc    37200
aatgccagcg cttcgttaat acagatgtag gtgttccaca gggtagccag cagcatcctg    37260
cgatgcagat ccggaacata atggtgcagg gcgctgactt ccgcgtttcc agactttacg    37320
aaacacggaa accgaagacc attcatgttg ttgctcaggt cgcagacgtt ttgcagcagc    37380
agtcgcttca cgttcgctcg cgtatcggtg attcattctg ctaaccagta aggcaacccc    37440
gccagcctag ccgggtcctc aacgacagga gcacgatcat gcgcacccgt ggccaggacc    37500
caacgctgcc cgagatgcgc cgcgtgcggc tgctggagat ggcggacgcg atggatatgt    37560
tctgccaagg gttggtttgc gcattcacag ttctccgcaa gaattgattg gctccaattc    37620
ttggagtggt gaatccgtta gcgaggtgcc gccggcttcc attcaggtcg aggtggcccg    37680
gctccatgca ccgcgacgca acgcggggag gcagacaagg tatagggcgg cgcctacaat    37740
ccatgccaac ccgttccatg tgctcgccga ggcggcataa atcgccgtga cgatcagcgg    37800
tccagtgatc gaagttaggc tggtaagagc cgcgagcgat ccttgaagct gtccctgatg    37860
gtcgtcatct acctgcctgg acagcatggc ctgcaacgcg ggcatcccga tgccgccgga    37920
agcgagaaga atcataatgg ggaaggccat ccagcctcgc gtcgcgaacg ccagcaagac    37980
gtagcccagc gcgtcggccg ccatgccggc gataatggcc tgcttctcgc cgaaacgttt    38040
ggtggcggga ccagtgacga aggcttgagc gagggcgtgc aagattccga ataccgcaag    38100
cgacaggccg atcatcgtcg cgctccagcg aaagcggtcc tcgccgaaaa tgacccagag    38160
cgctgccggc acctgtccta cgagttgcat gataaagaag acagtcataa gtgcggcgac    38220
gatagtcatg ccccgcgccc accggaagga gctgactggg ttgaaggctc tcaagggcat    38280
cggtcgagga caggnnngga tcctta                                         38306

<210> SEQ ID NO 6
<211> LENGTH: 40
<212> TYPE: DNA
<213> ORGANISM: Homo sapiens

<400> SEQUENCE: 6 gcgggggta ccaccatggc tgccatctct acttccatcc                            40

<210> SEQ ID NO 7
<211> LENGTH: 60
<212> TYPE: DNA
<213> ORGANISM: Homo sapiens

<400> SEQUENCE: 7
gcggggctcg agtcacttgt cgtcgtcgtc cttatagtca accacagagt gatcattgct     60

<210> SEQ ID NO 8
<211> LENGTH: 1095
<212> TYPE: DNA
<213> ORGANISM: Homo sapiens

<400> SEQUENCE: 8
atggctgcca tctctacttc catccctgta atttcacagc cccagttcac agccatgaat     60
```

```
                                    -continued gaaccacagt gcttctacaa cgagtccatt gccttctttt ataaccgaag tggaaagcat      120
cttgccacag aatggaacac agtcagcaag ctggtgatgg gacttggaat cactgtttgt      180
atcttcatca tgttggccaa cctattggtc atggtggcaa tctatgtcaa ccgccgcttc      240
cattttccta tttattacct aatggctaat ctggctgctg cagacttctt tgctgggttg      300
gcctacttct atctcatgtt caacacagga cccaatactc ggagactgac tgtcagcaca      360
tggctccttc gtcagggcct cattgacacc agcctgacgg catctgtggc caacttactg      420
gctattgcaa tcgagaggca cattacggtt ttccgcatgc agctccacac acggatgagc      480
aaccggcggg tagtggtggt cattgtggtc atctggacta tggccatcgt tatgggtgct      540
atacccagtg tgggctggaa ctgtatctgt gatattgaaa attgttccaa catggcaccc      600
ctctacagtg actcttactt agtcttctgg gccattttca acttggtgac ctttgtggta      660
atggtggttc tctatgctca catctttggc tatgttcgcc agaggactat gagaatgtct      720
cggcatagtt ctggacccg gcggaatcgg gataccatga tgagtcttct gaagactgtg      780
gtcattgtgc ttgggccttt tatcatctgc tggactcctg gattggtttt gttacttcta      840
gacgtgtgct gtccacagtg cgacgtgctg gcctatgaga aattcttcct tctccttgct      900
gaattcaact ctgccatgaa ccccatcatt tactcctacc gcgacaaaga aatgagcgcc      960
acctttaggc agatcctctg ctgccagcgc agtgagaacc ccaccggccc cacagaaggc     1020
tcagaccgct cggcttcctc cctcaaccac accatcttgg ctggagttca cagcaatgac     1080
cactctgtgg tttag                                                      1095
```